US009447224B2

(12) United States Patent
Izumi et al.

(10) Patent No.: US 9,447,224 B2
(45) Date of Patent: Sep. 20, 2016

(54) URETHANE (METH) ACRYLATE MONOMER AND PRODUCTION PROCESS THEREOF

(75) Inventors: Shinobu Izumi, Shunan (JP); Mitsuyoshi Sando, Shunan (JP); Junji Takenaka, Shunan (JP); Junji Momoda, Shunan (JP)

(73) Assignee: TOKUYAMA CORPORATION, Shunan-Shi (JP)

( * ) Notice: Subject to any disclaimer, the term of this patent is extended or adjusted under 35 U.S.C. 154(b) by 757 days.

(21) Appl. No.: 13/509,829

(22) PCT Filed: Nov. 16, 2010

(86) PCT No.: PCT/JP2010/070752
§ 371 (c)(1),
(2), (4) Date: May 15, 2012

(87) PCT Pub. No.: WO2011/059117
PCT Pub. Date: May 19, 2011

(65) Prior Publication Data
US 2012/0228567 A1 Sep. 13, 2012

(30) Foreign Application Priority Data
Nov. 16, 2009 (JP) .................................. 2009-261215

(51) Int. Cl.
| C08G 18/10 | (2006.01) |
| C08G 18/67 | (2006.01) |
| C08G 18/62 | (2006.01) |
| C08G 18/73 | (2006.01) |
| C08G 18/75 | (2006.01) |
| C07C 271/20 | (2006.01) |
| C07C 271/24 | (2006.01) |

(52) U.S. Cl.
CPC ............ C08G 18/672 (2013.01); C07C 271/20 (2013.01); C07C 271/24 (2013.01); C08G 18/62 (2013.01); C08G 18/6229 (2013.01); C08G 18/673 (2013.01); C08G 18/6725 (2013.01); C08G 18/73 (2013.01); C08G 18/755 (2013.01); C07C 2101/14 (2013.01)

(58) Field of Classification Search
CPC .............. C08G 18/6229; C08G 18/62; C08G 18/6725; C08G 18/673; C08G 18/82
See application file for complete search history.

(56) References Cited

U.S. PATENT DOCUMENTS

| 4,358,476 A * | 11/1982 | Zimmer ................... B05D 5/06 |
| | | 427/494 |
| 4,691,045 A * | 9/1987 | Fukuchi et al. ............ 560/185 |
| 6,743,879 B1 * | 6/2004 | Smith ................... C08F 220/36 |
| | | 525/123 |

FOREIGN PATENT DOCUMENTS

| DE | 298 25 066 U1 | 7/2004 |
| JP | 10-158371 A | 6/1998 |
| JP | 2000-34334 A | 2/2000 |
| JP | 2001-117226 A | 4/2001 |
| JP | 2004-10489 A | 1/2004 |
| JP | 2005-331932 A | 12/2005 |
| JP | 2006-201546 A | 8/2006 |
| JP | 2007-63189 A | 3/2007 |
| JP | 2007063189 A * | 3/2007 |

OTHER PUBLICATIONS

International Search Report issued in PCT/JP2010/070752, mailed on Mar. 8, 2011.
International Preliminary Report on Patentability, and Translation of Written Opinion of the International Searching Authority, dated Jun. 21, 2012, for International Application No. PCT/JP2010/070752 (Forms PCT/IB/338, PCT/IB/373 and PCT/ISA/237).
Atai, M. et al., "Synthesis, characterization, shrinkage and curing kinetics of a new low-shrinkage urethane dimethacrylate monomer for dental applications," Dental Materials, Jun. 16, 2007, vol. 23, No. 8, pp. 1030-1041.
Extended European Search Report for Appl. No. 10830069.0 dated Jun. 27, 2014.
Moszner, N. et al, "A partially aromatic urethane dimethacrylate as a new substitute for Bis-GMA in restorative composites," Dental Materials, Mar. 19, 2008, vol. 24, No. 5, pp. 694-699.
Moszner, N. et al, "Synthesis and polymerisation of new multifunctional urethane methacrylates," Die Angewandte Makromolekulare Chemie, Mar. 1, 1999, vol. 265, pp. 31-35.
Catalog "Gohselac", a front cover, pp. 5 and 6, and a back cover, issued by the Nippon Synthetic Chemical Industry Co., Ltd., in Jun. 1986.

(Continued)

Primary Examiner — Michael L Leonard
(74) Attorney, Agent, or Firm — Birch, Stewart, Kolasch & Birch, LLP

(57) ABSTRACT

A process of producing a urethane (meth)acrylate monomer having a low acid value and a low content of a hardly soluble high-molecular weight impurity which is crosslinked high-dimensionally, comprising the steps of:

(1) contacting a first solution containing a urethane (meth) acrylate monomer having an acid value of more than 0.2 mgKOH/g and an organic solvent to a water-containing adsorbent capable of adsorbing an acid component to obtain a second solution containing a urethane (meth) acrylate monomer having an acid value of not more than 0.2 mgKOH/g, the organic solvent and more than 5,000 ppm (mass) of water based on the urethane (meth)acrylate monomer;

(2) contacting the second solution to a dehydrating agent to obtain a third solution containing not more than 5,000 ppm (mass) of water based on the urethane (meth)acrylate monomer; and (3) removing the organic solvent from the third solution.

11 Claims, No Drawings

(56) References Cited

OTHER PUBLICATIONS

Catalog "Shiko", a front cover, pp. 3-10, 13, 14 and a back cover, issued by the Nippon Synthetic Chemical Industry Co., Ltd., in Apr. 2011.

Information Offer Form submitted by a third party (i.e., pre-grant third party submission) against corresponding Japanese patent application No. 2011-540586.

Table to summarize Examples disclosed in corresponding Japanese patent application No. 2011-540586, which is attached to Information Offer Form submitted by a third party against corresponding Japanese patent application.

Technical information of UV Curable Urethane acrylate resin "Shiko", retrieved from the website of the Nippon Synthetic Chemical Industry Co., Ltd, (http://www.nichigo.co.jp/spp/products/shiko.html) on Oct. 20, 2014.

* cited by examiner

URETHANE (METH) ACRYLATE MONOMER AND PRODUCTION PROCESS THEREOF

TECHNICAL FIELD

The present invention relates to a urethane (meth) acrylate monomer and a production process thereof. In the present invention, the term "urethane (meth) acrylate monomer" means both a urethane acrylate monomer and a urethane methacrylate monomer.

BACKGROUND ART

Monomers which are curable with heat or an active energy line and used in coating compositions include monomers having a (meth) acryloyl group (acryloyl group or methacryloyl group) in the molecule, such as urethane (meth) acrylate, polyester (meth) acrylate and epoxy (meth) acrylate. Since urethane (meth) acrylate monomers out of these can be synthesized from a compound containing an isocyanate group and a compound containing a hydroxyl group or a carboxyl group, a wide variety of molecular designs are made possible by combining these compounds. Therefore, the urethane (meth) acrylate monomers are widely used as materials for coating agents, adhesives, coating compositions and plastic products.

Since the urethane (meth) acrylate monomers are synthesized from a compound containing an isocyanate group and a compound containing a hydroxyl group or a carboxyl group as described above, an acid component and a by-produced high-molecular weight impurity may remain in the obtained urethane (meth) acrylate monomers. This acid component may or may not cause a problem according to use purpose. For example, when a urethane (meth) acrylate monomer is used in a photosensitive resin, it does not cause a problem. For application in a photosensitive resin, a urethane (meth)acrylate monomer having an acid value of not less than 5 mgKOH/g is preferably used (refer to JP-A 2005-331932 and JP-A 2006-201546). Therefore, a large number of urethane (meth)acrylate monomers having a high acid value are available on the market.

However, the acid component contained in the urethane (meth)acrylate monomer may react with another monomer component or an additive component, thereby causing the coloration or discoloration of the obtained polymer in application fields other than photosensitive resins. A urethane (meth)acrylate monomer containing a large amount of an acid component and having a high acid value may deteriorate in storage stability, and there is room for improvement in this respect.

For example, for application in optical materials such as lenses, the requirements for a cured product include high strength and a small shrinkage factor. To meet these requirements, use of a urethane (meth)acrylate monomer as a component of a composition for the cured product is effective. However, the acid component contained in the urethane (meth)acrylate monomer causes the degradation of weather resistance. When the optical material is a photochromic lens material, the acid component may cause the deterioration of a photochromic dye. Therefore, there is also room for improvement in this respect.

Since the high-molecular weight impurity contained in the urethane (meth)acrylate monomer increases the viscosity of the monomer, it may make filtration operation at the time of production cumbersome and complicate. Further, this high-molecular weight impurity may become the cause of a deposit and may degrade the performance of the urethane (meth)acrylate monomer when the monomer is used in a primer.

To cope with these problems, there is known a method of reducing the amount of a high-molecular weight impurity by dissolving a urethane (meth)acrylate monomer containing a high-molecular weight impurity in a water-soluble organic solvent and contacting the obtained solution to an adsorbent such as activated carbon, a synthetic resin adsorbent or activated alumina (refer to JP-A 2007-63189). In this method, it is considered that particularly when activated alumina is used, an acid component can be also removed efficiently.

However, according to studies conducted by the inventors of the present invention, it was found that when activated alumina is used, there is a case where the high-molecular weight impurity cannot be removed completely though the acid component can be removed. It is disclosed in Examples of JP-A 2007-63189 that the content of a high-molecular weight impurity becomes 0.3% when a solution obtained by dissolving a urethane (meth)acrylate monomer containing 0.6% of a high-molecular weight impurity in ethanol is contacted to activated alumina. It was found that when a solution of a urethane (meth)acrylate monomer containing no high-molecular weight impurity is contacted to activated alumina, the activated alumina is filtered, and the filtrate is concentrated to produce urethane (meth) acrylate having a reduced acid value according to this method, about 0.3% of a high-molecular weight impurity is contained. This shows that a high-molecular weight impurity is newly produced when the urethane (meth)acrylate monomer is contacted to activated alumina as an adsorbent according to the method of JP-A 2007-63189.

DISCLOSURE OF THE INVENTION

It is therefore an object of the present invention to provide a urethane (meth)acrylate monomer having a low acid value, a low content of a high-molecular weight impurity and excellent storage stability and a process capable of producing the urethane (meth)acrylate monomer efficiently.

The inventors of the present invention conducted intensive studies to attain the above object. To begin with, in order to reduce the amount of an acid component and the amount of a high-molecular weight impurity, they investigated the cause of increasing the amount of the high-molecular weight impurity after an adsorbent is contacted to a urethane (meth)acrylate monomer containing no high-molecular weight impurity. When they checked the difference in effect between different adsorbents, they found that when activated alumina was used, the acid component could be removed like vapor but the high-molecular weight impurity could not be removed completely whereas when activated carbon was used, the acid component could not be adsorbed but the amount of the high-molecular weight impurity could be reduced. When the difference in function between the activated carbon and the activated alumina is taken into account, it is considered that the activated alumina has excellent adsorption ability for the acid component since it contains crystal water but this crystal water is involved in the by-production of a high-molecular weight impurity. Meanwhile, the results of studies conducted by the inventors of the present invention show that there is a connection between the amount of water contained in the solution after a treatment with an adsorbent and the amount of the high-molecular weight impurity produced and that the production of the high-molecular weight impurity can be suppressed by reducing the amount of water to a predetermined value or less. The present invention was accomplished based on this finding.

That is, according to the present invention, firstly, there is provided a urethane (meth)acrylate monomer having a water content of not more than 2,000 ppm (mass) and an acid value of not more than 0.2 mgKOH/g. The content of an insoluble component in a solution of 1 mass % of the urethane (meth)acrylate monomer in tetrahydrofuran is not more than 0.1 mass % based on the urethane (meth)acrylate monomer and the content of a high-molecular weight component having an average molecular weight which is 3 times or more that of the urethane (meth)acrylate monomer is less than 0.3 mass %.

Further, according to the present invention, secondly, there is provided a process of producing the above urethane (meth)acrylate monomer, comprising the steps of:

(1) contacting a first solution containing a urethane (meth) acrylate monomer having an acid value of more than 0.2 mgKOH/g and an organic solvent to a water-containing adsorbent capable of adsorbing an acid component to obtain a second solution containing a urethane (meth) acrylate monomer having an acid value of not more than 0.2 mgKOH/g, the organic solvent and more than 5,000 ppm (mass) of water based on the urethane (meth)acrylate monomer;

(2) contacting the second solution to a dehydrating agent to obtain a third solution containing a urethane (meth) acrylate monomer having an acid value of not more than 0.2 mgKOH/g, the organic solvent and not more than 5,000 ppm (mass) of water based on the urethane (meth) acrylate monomer; and (3) removing the organic solvent from the third solution.

In the above process, preferably, an organic solvent containing no active hydrogen is used as the organic solvent.

Further, the water-containing adsorbent capable adsorbing an acid component is an inorganic adsorbent containing crystal water or adhesive water.

In the present invention, the content of the high-molecular weight component is a peak area % obtained by gel permeation chromatography (GPC) measurement which will be described in detail hereinafter. In the present invention, the above "high-molecular weight component" may be referred to as "high-molecular weight impurity". The above amount of water is based on the mass of the urethane (meth) acrylate monomer.

BEST MODE FOR CARRYING OUT THE INVENTION

According to the process of the present invention, it is possible to obtain a urethane (meth)acrylate monomer having a lower acid value from a urethane (meth)acrylate monomer having an acid value of more than 0.2 mgKOH/g. The process is described step by step hereinunder.

<Urethane (Meth)Acrylate Monomer Having a Water Content of not More than 2,000 ppm (mass) and an Acid Value of not More than 0.2 mgKOH/g>

The preferred urethane (meth)acrylate monomer in the present invention may be represented by the following formula (I).

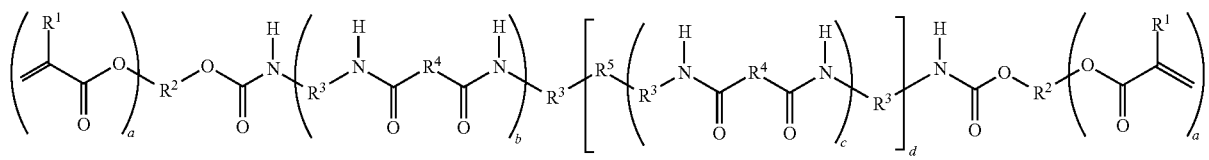

(1)

(In the above formula, a's are each independently an integer of 1 to 3, b, c and d are each independently an integer of 0 to 100, $R^1$ is a hydrogen atom or methyl group, $R^2$ is a divalent to tetravalent aliphatic hydrocarbon group which may have a substituent, $R^3$ is a divalent organic residue selected from a divalent group having an aromatic ring, a divalent group having an aliphatic ring and an alkylene group, $R^4$ is a divalent organic residue selected from a divalent group having a polyether structure, a divalent group having a polycarbonate structure and a divalent group having a polyester structure, and $R^5$ is a divalent group having a urea bond or a divalent group having a urethane bond.)

In the above formula (I), $R^2$ is a divalent to tetravalent aliphatic hydrocarbon group which may have a substituent. The aliphatic hydrocarbon group is, for example, a linear or branched aliphatic hydrocarbon group having 1 to 10 carbon atoms. Examples of the substituent for the aliphatic hydrocarbon group include an alkyl group having 1 to 4 carbon atoms, alkoxy group having 1 to 4 carbon atoms and phenoxy group. The substituent is preferably a methyl group, methoxy group or phenoxy group.

Preferred examples of the divalent to tetravalent aliphatic hydrocarbon group include alkylene groups such as methylene group, ethylene group, propylene group and butylene group, and aliphatic hydrocarbon groups represented by the following formulas because their raw materials are easily acquired.

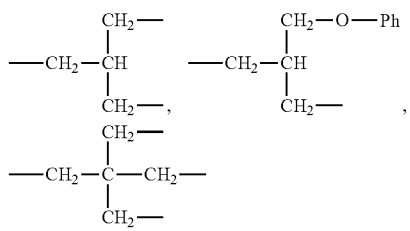

In the above formula (I), $R^3$ is a divalent organic residue selected from a divalent group having an aromatic ring, a divalent group having an aliphatic ring and an alkylene group. A description is subsequently given of the divalent group represented by $R^3$.

Divalent Group Having an Aromatic Ring

Examples of the aromatic ring include benzene, biphenyl, diphenylmethane and naphthalene. The bond of the divalent group may be attached to the aromatic ring directly or via a methylene group. The aromatic ring may or may not have a substituent. Preferred divalent groups having an aromatic ring are represented by the following formulas.

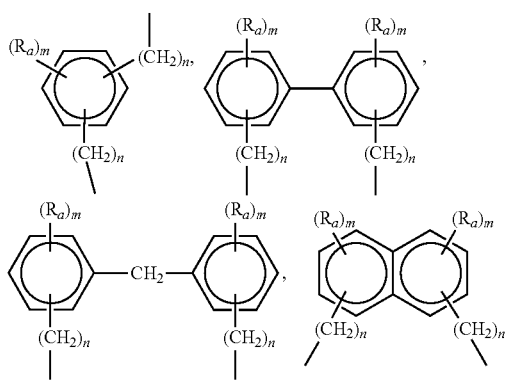

(In the above formulas, $R_a$ is an alkyl group having 1 to 4 carbon atoms or alkoxy group having 1 to 4 carbon atoms, m is an integer of 0 to 3 which indicates the number of substituent $R_a$'s, and n is an integer of 0 or 1.)

Out of the divalent groups having an aromatic ring represented by the above formulas, groups represented by the following formulas are particularly preferred.

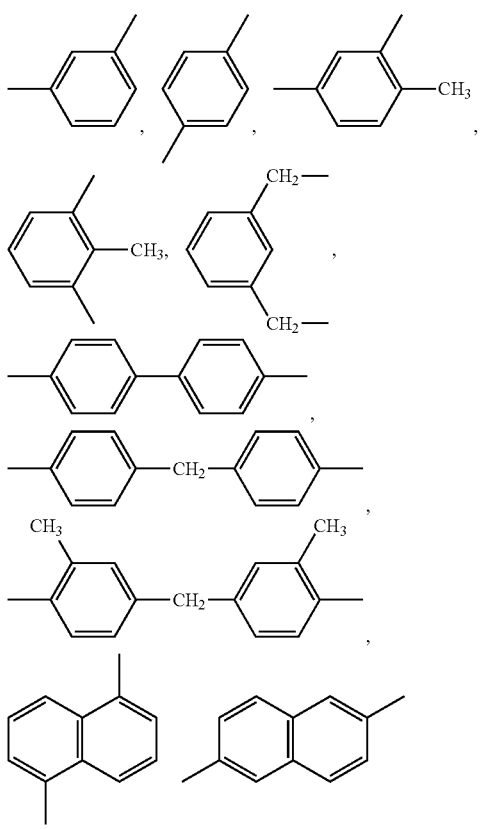

Divalent Group Having an Aliphatic Ring

Examples of the aliphatic ring include cyclohexane, hydrogenated biphenyl, hydrogenated diphenylmethane and bicyclo ring. The bond of the divalent group may be attached to the aliphatic ring directly or via a methylene group. The aliphatic ring may or may not have a substituent. Preferred divalent groups having an aliphatic ring are represented by the following formulas.

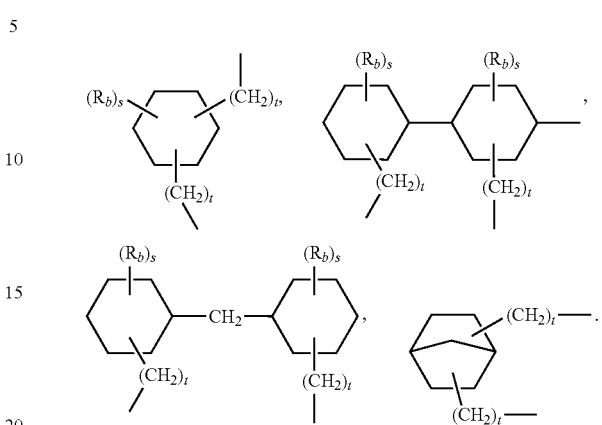

(In the above formulas, $R_b$ is an alkyl group having 1 to 4 carbon atoms or alkoxy group having 1 to 4 carbon atoms, s is an integer of 0 to 3 which indicates the number of substituent $R_b$'s, and t is 0 or 1.)

Out of the divalent groups having an aliphatic ring represented by the above formulas, groups represented by the following formulas are particularly preferred.

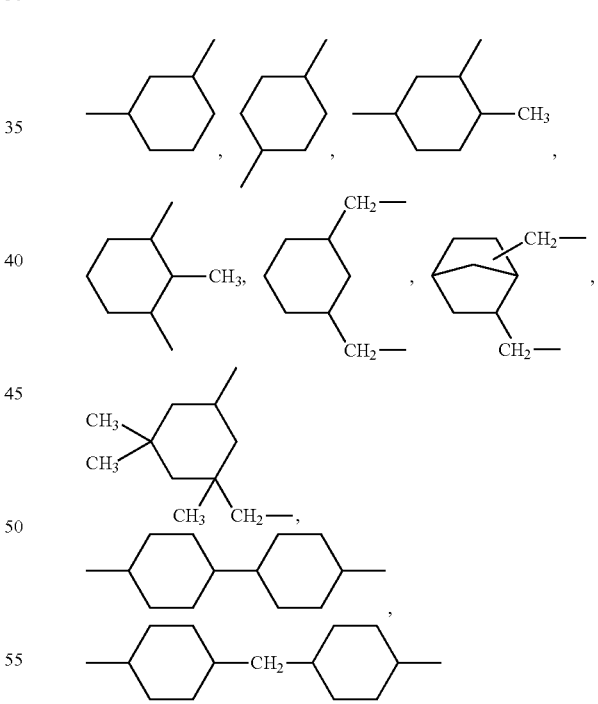

Alkylene Group

The alkylene group is preferably a linear or branched alkylene group having 1 to 10 carbon atoms and may have one or more methyl groups. A linear or branched alkylene group having 1 to 6 carbon atoms is more preferred, as exemplified by methylene group, ethylene group, propylene group, butylene group, pentamethylene group, hexamethylene group and the following groups.

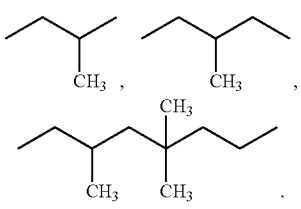

In the above formula (I), $R^4$ is a divalent organic residue selected from a divalent group having a polyether structure, a divalent group having a polycarbonate structure and a divalent group having a polyester structure. A description is subsequently given of the divalent groups represented by $R^4$.

Divalent Group Having a Polyether Structure

This is a group derived from a polyether polyol compound or a polyalkylene polyol compound, preferably a divalent group represented by the following formula.

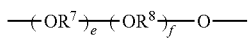

In the above formula, $R^7$ and $R^8$ are each independently an alkylene group having 1 to 10 carbon atoms, and e and f are each independently an integer of 0 to 50 but cannot be 0 at the same time. $R^7$ and $R^8$ are each preferably an alkylene group having 1 to 6 carbon atoms, as exemplified by methylene group, ethylene group, propylene group, butylene group, pentamethylene group and hexamethylene group. e and f are each an integer of preferably 0 to 20, particularly preferably 0 to 10.

Divalent Group Having a Polycarbonate Structure

This is a group derived from a polycarbonate polyol compound, preferably a divalent group represented by the following formula.

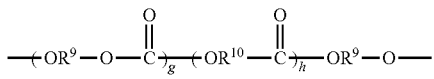

In the above formula, $R^9$ and $R^{10}$ are each independently a divalent hydrocarbon group having 1 to 20 carbon atoms, g is an integer of 1 to 50, and h is an integer of 0 to 50. $R^9$ and $R^{10}$ are each preferably a divalent group derived from an alkylene group having 1 to 6 carbon atoms or a bisphenol having 13 to 20 carbon atoms, as exemplified by methylene group, ethylene group, propylene group, butylene group, pentamethylene group, hexamethylene group and groups represented by the following formulas.

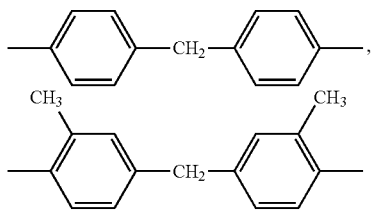

g is an integer of preferably 1 to 20, particularly preferably 1 to 10. h is an integer of preferably 0 to 20, particularly preferably 0 to 10.

Divalent Group Having a Polyester Structure

This is a group derived from a polyester polyol compound, preferably a divalent group represented by the following formula.

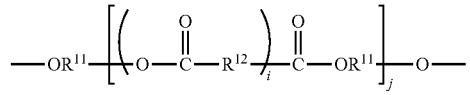

In the above formula, $R^{11}$ and $R^{12}$ are each independently an alkylene group having 1 to 10 carbon atoms, i is an integer of 0 or 1, and j is an integer of 1 to 50.

$R^{11}$ and $R^{12}$ are each preferably an alkylene group having 1 to 6 carbon atoms, as exemplified by methylene group, ethylene group, propylene group, butylene group, pentamethylene group and hexamethylene group. j is an integer of preferably 1 to 20, particularly preferably 1 to 10.

In the above formula (I), $R^5$ is a divalent group having a urea bond or a divalent group having a urethane bond. A description is subsequently given of the divalent groups represented by $R^5$.

Divalent Group Having a Urea Bond

This is a group having a urea bond (—NH—C(=O)—NH—) in the molecule, preferably a group represented by the following formula.

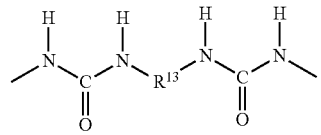

(In the above formula, $R^{13}$ is a divalent hydrocarbon group.)

In the above formula, the group represented by $R^{13}$ is a divalent hydrocarbon group having 1 to 20 carbon atoms, and preferred examples thereof are the same as those enumerated for $R^3$. Out of these, it is preferably a divalent group having an aliphatic ring or an alkylene group having 1 to 10 carbon atoms.

Divalent Group Having a Urethane Bond

This is a group having a urethane bond (—NH—C(=O)O—) in the molecule, preferably a group represented by the following formula.

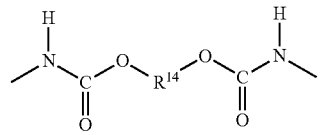

(In the above formula, $R^{14}$ is a divalent hydrocarbon group.)

In the above formula, the group represented by $R^{14}$ is a divalent hydrocarbon group having 1 to 20 carbon atoms, and preferred examples thereof are the same as those enumerated for $R^3$. Out of these, it is preferably a divalent group having an aliphatic ring or an alkylene group having 1 to 10 carbon atoms. The urethane (meth)acrylate monomer preferably obtained in the present invention is represented by the above formula (I) and may contain a 2,2,6,6-tetramethylpiperidine skeleton or a 2,6-di-tert-butylphenol skeleton in the molecule.

<Urethane (Meth) Acrylate Monomer Having an Acid Value of More than 0.2 mgKOH/g>

The urethane (meth)acrylate monomer used as a raw material in the process of the present invention has an acid value of more than 0.2 mgKOH/g, and a commercially available product thereof may also be used. The urethane (meth)acrylate monomer may be produced by a known process. The urethane (meth)acrylate monomer having an acid value of more than 0.2 mgKOH/g may be simply referred to as "raw material urethane monomer" hereinafter.

According to the process of the present invention, it is possible to reduce the acid value of a urethane (meth) acrylate monomer having an acid value of more than 0.2 mgKOH/g to not more than 0.2 mgKOH/g. Although the upper limit of the acid value of the raw material urethane monomer is not particularly limited if it exceeds 0.2 mgKOH/g, when the production and acquisition ease of an ordinary urethane (meth)acrylate monomer are taken into consideration, the upper limit is about 30 mgKOH/g. The acid value of the raw material urethane monomer which can be advantageously used in the process of the present invention is preferably more than 0.2 mgKOH/g to not more than 25 mgKOH/g, more preferably more than 0.2 mgKOH/g to not more than 20 mgKOH/g. Particularly when an inorganic adsorbent containing crystal water or adhesive water is used in the step (1), if the acid value of the raw material urethane monomer is too high, there is a case where the acid value cannot be reduced. Therefore, the raw material urethane monomer used in this case preferably has an acid value of more than 0.2 mgKOH/g to not more than 10 mgKOH/g.

To produce a urethane (meth)acrylate monomer from a raw material compound for the production of a urethane, an acid or a salt thereof is generally used as a catalyst, as exemplified by inorganic acids such as hydrochloric acid, sulfuric acid and nitric acid; organic acids such as sulfonic acid, oxyacid and carboxylic acid; and metal salts of an organic acid such as n-butyltin dilaurate, copper naphthenate, zinc naphthenate and tri-n-butyltin chloride. Therefore, the acid value of the synthesized urethane (meth)acrylate monomer becomes high because an acid component derived from the catalyst remains in the monomer. (Meth)acrylic acid derived from a hydroxyalkyl (meth)acrylate compound as a raw material compound for the production of a urethane also remains in the urethane (meth)acrylate monomer, thereby increasing the acid value. Since the urethane (meth) acrylate monomer contains an acid component derived from the catalyst and an acid component such as (meth)acrylic acid as impurities, the acid value of the urethane (meth) acrylate monomer (raw material urethane monomer) exceeds 0.2 mgKOH/g. When the urethane (meth)acrylate monomer is used as a raw material of a photosensitive resin, a urethane (meth)acrylate monomer having a high acid value is used. Therefore, urethane (meth)acrylate monomers having an acid value of 10 to 50 mgKOH/g are available on the market.

It is often desired that a cured product obtained by polymerizing a urethane (meth)acrylate monomer should not be colored even when it is used for a long time. To meet this, the raw material urethane monomer is preferably synthesized from an alicyclic isocyanate or an aliphatic isocyanate. This urethane (meth)acrylate monomer is generally called "non-yellow type". When a raw material urethane monomer having an acid value of more than 0.2 mgKOH/g is used, the process of the present invention is not particularly limited. When the above urethane (meth)acrylate monomer synthesized from an alicyclic isocyanate or an aliphatic isocyanate is used, the process of the present invention can be advantageously employed.

Out of raw material urethane monomers, a raw material urethane monomer having an acryloyl group readily causes a Michael addition reaction to produce a high-molecular weight impurity. Therefore, a urethane (meth)acrylate monomer synthesized by using a hydroxyalkyl acrylate, specifically a raw material urethane monomer synthesized by using 2-hydroxyethyl acrylate, 2-hydroxypropyl acrylate or 2-hydroxy-3-phenoxypropyl acrylate is preferably used.

The process of the present invention can be advantageously employed when a raw material urethane monomer having a plurality of (meth)acryloyl groups in one molecule is used, more specifically when a raw material urethane monomer having 2 to 6 (meth)acryloyl groups in one molecule is used. As described above, it is considered that a raw material urethane monomer having a plurality of (meth) acryloyl groups readily causes a Michael addition reaction to produce a high-molecular weight impurity. Therefore, the process of the present invention provides an excellent effect when the above raw material urethane monomer is used.

Further, the process of the present invention can be advantageously employed when a raw material urethane monomer having a molecular weight of 300 to 100,000, preferably 300 to 50,000, more preferably 300 to 5,000 is used. The molecular weight of this raw material urethane monomer is a value calculated from the type of the atom constituting the monomer. The raw material urethane monomer having the above molecular weight has high viscosity. According to an estimate by the inventors of the present invention, it is fairly possible that when the organic solvent is removed, a Michael addition reaction occurs between molecules, thereby producing a high-molecular weight impurity which is crosslinked high-dimensionally. Therefore, it is considered that when the solvent is gradually removed and the high-molecular weight impurity is produced from the raw material urethane monomer having high viscosity, the viscosity becomes high drastically with the result that a post-treatment becomes more complicated. Since the process of the present invention can suppress the production of the high-molecular weight impurity, it provides an excellent effect when the raw material urethane monomer having the above molecular weight is used.

In the present invention, the raw material urethane monomer has a urethane bond and a (meth)acryloyl group in the molecule and is synthesized from a combination of a polyisocyanate, a hydroxyalkyl (meth)acrylate and optionally a polyol compound and a polyamine compound, and a commercially available urethane (meth) acrylate monomer may also be used. Commercially available raw material urethane monomers are given below.

(1) Urethane (meth)acrylate monomers manufactured by Shin Nakamura Chemical Co., Ltd. such as NK Oligo U-4HA (non-yellowed type, 4 acryloyl groups, molecular weight of about 600), NK Oligo U-4H (non-yellowed type, 4 methacryloyl groups, molecular weight of about 600), NK Oligo U-6HA (non-yellowed type, 6 acryloyl groups, molecular weight of about 1,000), NK Oligo U-6H (non-yellowed type, 6 methacryloyl groups, molecular weight of about 1,000), NK Oligo U-108A (non-yellowed type, 2 acryloyl groups, molecular weight of about 1,600), NK Oligo U-122A (non-yellowed type, 2 acryloyl groups, molecular weight of about 1,100), NK Oligo U-2PPA (non-yellowed type, 2 acryloyl groups, molecular weight of about 500), NK Oligo UA-5201 (non-yellowed type, 2 acryloyl groups, molecular weight of about 1,000), NK Oligo UA-1101H (6 acryloyl groups, molecular weight of about 1,800), NK Oligo UA-6LPA (6 acryloyl groups, molecular weight of about 800), NK Oligo UA-412A (2 acryloyl groups, molecular weight of about 4,700), NK Oligo UA-4200 (2 acryloyl groups, molecular weight of about 1,300) and NK Oligo UA-4400 (2 acryloyl groups, molecular weight of about 1,300), (2) urethane (meth)acrylate monomers manufactured by KYOEISYA CHEMICAL Co., Ltd. such as AH-600 (non-yellowed type, 2 acryloyl groups, molecular weight of about 600), AI-600 (non-yellowed type, 2 acryloyl groups, molecular weight of about 600), UA-101H (non-yellowed type, 4 methacryloyl groups, molecular weight of about 600), UA-101I (non-yellowed type, 4 methacryloyl groups, molecular weight of about 700), UA-306H (non-yellowed type, 6 acryloyl groups, molecular weight of about 700) and UA-306I (non-yellowed type, 6 acryloyl groups, molecular weight of about 800), and (3) urethane (meth)acrylate monomers manufactured by Daicel Cytec Co., Ltd. such as Ebecry1270 (non-yellowed type, 2 acryloyl groups, molecular weight of about 1,500), Ebecry1210 (2 acryloyl groups, molecular weight of about 1,500), Ebecry11290K (non-yellowed type, 6 acryloyl groups, molecular weight of about 1,000), Ebecry15129 (non-yellowed type, 6 acryloyl groups, molecular weight of about 800), Ebecryl-4858 (non-yellowed type, 2 acryloyl groups, molecular weight of about 600), Evecry18210 (non-yellowed type, 4 acryloyl groups, molecular weight of about 600), Ebecry18402 (non-yellowed type, 2 acryloyl groups, molecular weight of about 1,000), Ebecry19270 (non-yellowed type, 2 acryloyl groups, molecular weight of about 1,000), Ebecry1230 (non-yellowed type, 2 acryloyl groups, molecular weight of about 5,000), Ebecry18201 (non-yellowed type, 3 acryloyl groups, molecular weight of about 2,100) and Ebecry18804 (non-yellowed type, 2 acryloyl groups, molecular weight of about 1,300).

The raw material urethane monomer has a high-molecular weight impurity content of preferably not more than 0.3 mass %, more preferably 0.0 mass % (detection limit of GPC measurement shown below). By using a raw material urethane monomer having a low content of a high-molecular weight impurity, the purity of the finally obtained product can be easily made high.

Further, the raw material urethane monomer preferably has a water content of not more than 2,000 ppm (mass). The lower limit of the water content is 0 ppm (mass) (detection limit of the measurement of water content shown below). Ordinary commercially available products have a water content within the above range.

The present invention reduces the acid value of the raw material urethane monomer which has an acid value of more than 0.2 mgKOH/g and further suppresses the production of a high-molecular weight impurity. To attain this object, the process of the present invention comprises the following steps:

(1) contacting a first solution comprising a urethane (meth)acrylate monomer having an acid value of more than 0.2 mgKOH/g and an organic solvent to a water-containing adsorbent capable of adsorbing an acid component to obtain a second solution comprising a urethane (meth)acrylate monomer having an acid value of not more than 0.2 mgKOH/g, the organic solvent and more than 5,000 ppm (mass) of water based on the urethane (meth)acrylate monomer, (2) contacting the above second solution to a dehydrating agent to obtain a third solution comprising a urethane (meth)acrylate monomer having an acid value of not more than 0.2 mgKOH/g, the organic solvent and not more than 5,000 ppm (mass) of water based on the urethane (meth) acrylate monomer; and (3) removing the organic solvent from the third solution. A description is subsequently given of each step.

<Step (1) of Reducing the Acid Value of the Raw Material Urethane Monomer to not More than 0.2 mgKOH/g>

In this step, the acid value of the above raw material urethane monomer is reduced to not more than 0.2 mgKOH/g. To reduce the acid value, the raw material urethane monomer is first dissolved in an organic solvent, and the obtained first solution is contacted to a water-containing adsorbent capable of adsorbing an acid component. A lower acid value after contact with the water-containing adsorbent is more preferred. That is, it is most preferred that the acid value measured by the method shown in the following examples should be 0 mgKOH/g. In consideration of the industrial-scale production of a urethane (meth)acrylate monomer, the acid value after contact with the water-containing adsorbent is not less than 0.01 mgKOH/g in most cases.

Organic Solvent Used in the First Solution

In the present invention, the organic solvent for dissolving the raw material urethane monomer is not particularly limited if it is a solvent which dissolves the raw material urethane monomer and does not react with the monomer. Specific examples of the organic solvent include alcohols having 1 to 4 carbon atoms; ketone solvents such as acetone, methyl ethyl ketone and methyl isobutyl ketone; ester solvents such as ethyl acetate, propyl acetate and butyl acetate; aromatic solvents such as benzene, toluene and xylene; ether solvents such as diethyl ether, butyl methyl ether, dipropyl ether, dibutyl ether, tetrahydrofuran and dioxane; aliphatic solvents such as hexane, heptane, cyclohexane and decahydronaphthalene; halogen solvents such as dichloromethane, chloroform and carbon tetrachloride; and glycol solvents such as ethylene glycol monomethyl ether acetate and propylene glycol monomethyl ether acetate.

In the present invention, since the step of reducing the water content is included in the step (2) which will be described hereinafter, water solubility in the organic solvent is preferably low. Further, an organic solvent containing no activated hydrogen is preferably used. Stated more specifically, an organic solvent which does not contain activated hydrogen and has a water solubility at 20° C. of not more than 20 vol % is preferred, and a nonaqueous organic solvent having a water solubility of not more than 10 vol % is preferably used. By using this organic solvent, water is easily removed and the production of a high-molecular weight impurity contained in the finally obtained urethane (meth)acrylate monomer is easily suppressed.

The organic solvent particularly preferably used in the present invention is selected from toluene, xylene, ethyl acetate, butyl acetate, methyl ethyl ketone, dichloromethane and chloroform. These organic solvents may be used alone or in combination of two or more.

The amount of the organic solvent is not particularly limited if it dissolves the raw material urethane monomer. However, when it is used in a larger amount than required, the yield per unit operation becomes low and the removal of the organic solvent takes time. Therefore, it is preferred that the amount of the organic solvent should be minimum that ensures that it can be dispersed. The specific amount of the organic solvent may be suitably determined according to the 5. type of the raw material urethane monomer and the type of the organic solvent. To enhance manipulation ease and suppress the production of the high-molecular weight impurity, the amount of the organic solvent is preferably 100 to 1,000 parts by mass, more preferably 100 to 500 parts by mass based on 100 parts by mass of the urethane (meth) acrylate monomer.

In the step (1), the raw material urethane monomer is dissolved in the above organic solvent and the obtained first solution is contacted to the water-containing adsorbent capable of adsorbing an acid component to reduce the acid value of the urethane (meth)acrylate monomer contained in the solution. According to this method, the water content of the second solution which is described below can be easily reduced and the production of the high-molecular weight impurity contained in the finally obtained urethane (meth) acrylate monomer can be easily suppressed.

A description is subsequently given of the method of reducing the acid value by means of the water-containing adsorbent.

Water-Containing Adsorbent

Any known adsorbent may be used as the water-containing adsorbent used in the above method without limitation if it is able to adsorb an acid component and contains water. Water may be contained as adhesive water or crystal water. Examples of the water-containing adsorbent include oxides and hydroxides of an alkali earth metal such as magnesium, calcium, strontium or barium; oxides and hydroxides of metals of the aluminum group such as aluminum and boron; and water-containing inorganic adsorbents comprising silicon oxide as the main component. Crystal water-containing inorganic adsorbents comprising magnesium oxide, aluminum oxide, silicon dioxide, magnesium hydroxide or aluminum hydroxide as the main component may be preferably used, and crystal water-containing inorganic adsorbents comprising aluminum oxide or aluminum hydroxide as the main component may be particularly preferably used as they have high acid component adsorption power.

Commercially available products of these water-containing adsorbents may be used. Commercially available products include Kyoward (registered trademark) series of Kyowa Chemical Co., Ltd. and Tomix AD series of Tomita Pharmaceutical Co., Ltd. Commercially available products of crystal water-containing inorganic adsorbents comprising aluminum oxide as the main component include Kyoward 300 (composition: $2.5MgO.Al_2O_3.nH_2O$ (n=0.5 to 3)) (of Kyowa Chemical Co., Ltd.), and Tomix-AD200 (composition: $Al_2O_3.nH_2O$ (n=0.5 to 3)), Tomix-AD300 (composition: $MgO.Al_2O_3.2SiO_2.nH_2O$ (n=0.5 to 3)) and Tomix-AD700 (composition: $Al_2O_3.10SiO_2.nH_2O$(N=0.1 to 2)) (of Tomita Pharmaceutical Co., Ltd.). Commercially available products of crystal water-containing inorganic adsorbents comprising aluminum hydroxide as the main component include Kyoward 200 (composition: $Al(OH)_3.nH_2O$ (n=0.5 to 3)) (of Kyowa Chemical Co., Ltd.), and Tomix-AD400 (composition: $Al(OH)_3.NaHCO_3. nH_2O$ (n=0.1 to 2)) (of Tomita Pharmaceutical Co., Ltd.). Commercially available products of crystal water-containing inorganic adsorbents comprising magnesium hydroxide as the main component include Kyoward 500 (composition: $Mg_6Al_2(OH)_{16}CO_3.nH_2O$ (n=1 to 5)) (of Kyowa Chemical Co., Ltd.). Commercially available products of crystal water-containing inorganic adsorbents comprising magnesium oxide as the main component include Kyoward 2000 (composition: $Mg_{0.7}Al_{0.3}O_{1.15}.nH_2O$ (=0.1 to 2)) (of Kyowa Chemical Co., Ltd.).

The water-containing adsorbent which can reduce the amount of the acid component efficiently contains crystal water. Although this adsorbent containing crystal water can reduce the amount of the acid component efficiently as it contains crystal water, water remains in the system (the second solution). Therefore, the amount of this water must be reduced in the subsequent step. When the above inorganic adsorbent is used, the organic solvent used in the first solution may be a water-soluble organic solvent having active hydrogen. To facilitate the reduction of the amount of water produced from this inorganic adsorbent, the organic solvent is preferably a solvent containing no active hydrogen, particularly preferably the above nonaqueous organic solvent.

Method of Reducing the Acid Value by Means of Water-Containing Adsorbent

In the present invention, the adsorption and removal of the acid component by the water-containing adsorbent capable of adsorbing an acid component are not particularly limited and can be carried out by contacting the first solution to the above water-containing adsorbent in accordance with a known method.

The amount of the water-containing adsorbent is not particularly limited and may be suitably determined according to the type of the water-containing adsorbent in use and the acid value of the raw material urethane monomer. Stated more specifically, the following range is preferred when the effect of the removal of the acid component, the removal of the water-containing adsorbent, the removal of water in the case of use of an inorganic adsorbent containing crystal water and the yield of the obtained urethane (meth)acrylate monomer are taken into consideration. More specifically, the amount of the water-containing adsorbent is preferably 0.1 to 50 parts by mass, more preferably 1 to 30 parts by mass based on 100 parts by mass of the urethane (meth)acrylate monomer.

As a specific treatment method when the water-containing adsorbent is used, the first solution may be contacted to the water-containing adsorbent by a known method. More specifically, it is preferred to contact them to each other while they are stirred and mixed together. The procedure for mixing together the first solution and the water-containing adsorbent upon contact is not particularly limited but generally, the water-containing adsorbent should be added to the first solution.

The temperature for contacting the first solution to the water-containing adsorbent is not particularly limited but preferably 0 to 70° C., more preferably 5 to 30° C. When the temperature at the time of contact falls within the above range, the amount of the acid component can be reduced fully and the amount of the high-molecular weight impurity can also be reduced.

The contact time is not particularly limited and may be a time during which the amount of the acid component can be reduced fully. For example, it is 30 minutes to 10 hours. This treatment time can be determined by collecting part of the treated solution and confirming that the acid value of the urethane (meth)acrylate monomer contained in the treated solution becomes not more than 0.2 mgKOH/g.

After this contact treatment, the water-containing adsorbent can be removed by a known method, for example, filtration or centrifugation.

In the present invention, the second solution is formed by contacting the above first solution to the water-containing adsorbent. According to studies conducted by the inventors of the present invention, it was confirmed that the obtained second solution must contain a certain amount or more of water in order to reduce the acid value of the urethane (meth)acrylate monomer to not more than 0.2 mgKOH/g in this treatment. It was also found that this water exerts an influence on the purity of the finally obtained urethane (meth)acrylate monomer and that the organic solvent must be removed after the amount of water is reduced.

The obtained second solution contains water due to the fact that the acid value of the urethane (meth)acrylate monomer is greatly reduced to not more than 0.2 mgKOH/g by the contact treatment between the first solution and the water-containing adsorbent. As a result, it was found that the second solution contains the urethane (meth)acrylate monomer and more than 5,000 ppm (mass) of water based on the urethane (meth)acrylate monomer besides the above organic solvent. The upper limit of the amount of water contained in this second solution is affected by the method of reducing the acid value of the raw material urethane monomer and the amount of the acid component but generally about 30,000 ppm (mass) based on the mass of the urethane (meth) acrylate monomer. To produce a urethane (meth)acrylate monomer having high purity most efficiently in the present invention, the amount of water contained in the second solution is preferably more than 5,000 ppm (mass) to not more than 20,000 ppm (mass), more preferably more than 5,000 ppm (mass) to not more than 15,000 ppm (mass) based on the urethane (meth) acrylate monomer. For example, even when an inorganic adsorbent containing crystal water is used for efficient production, the amount of water can be adjusted to more than 5,000 ppm (mass) to 15,000 ppm (mass) based on the urethane (meth)acrylate monomer.

A description is subsequently given of the step (2) of contacting the second solution obtained in the step (1) to a dehydrating agent to reduce the amount of water.

<Step (2) of Reducing the Amount of Water Contained in Second Solution>

The second solution obtained in the above step (1) contains the organic solvent, a urethane (meth)acrylate monomer having an acid value of not more than 0.2 mgKOH/g and more than 5,000 ppm (mass) of water based on the urethane (meth)acrylate monomer.

Even when a monomer having a (meth)acryloyl group contains water in the purification of the monomer, water can be generally removed by a method such as distillation under reduced pressure. Particularly when a solvent which easily co-boils with water such as toluene is used for purification and the organic solvent is distilled under reduced pressure, water can be removed at the same time. However, it was found that when the organic solvent is removed while water remains in the case of the urethane (meth)acrylate monomer, a high-molecular weight impurity is produced.

Although the cause of producing this high-molecular weight impurity is unknown, when a urethane (meth)acrylate monomer having an increased content of the high-molecular weight impurity is analyzed by FT-IR, it is conceivable that the following is the cause. That is, when more than 5,000 ppm (mass) of water is contained in the second solution and the organic solvent is to be distilled off, if the organic solvent is a solvent which co-boils with water, the probability of contact between the urethane (meth) acrylate monomer and water is assumed to be high. Although it is conceivable that the residual acid component has an influence on this, it is considered that this water hydrolyzes the urethane moiety of the urethane (meth) acrylate monomer to produce an amine with the result that the amine and the (meth) acryloyl group are crosslinked with each other through a Michael addition reaction to produce the high-molecular weight impurity. This tendency becomes remarkable when the urethane (meth)acrylate monomer is a urethane acrylate monomer having an acryloyl group.

It is assumed from this result that even when the urethane (meth)acrylate monomer is purified by using the activated alumina of JP-A 2007-63189, the amount of the high-molecular weight impurity contained originally can be reduced by activated alumina but water generated by this treatment produces a new high-molecular weight impurity with the result that 0.3 mass % of the high-molecular weight impurity is contained.

It is understood from above that, in the present invention, before the organic solvent is removed from the second solution, the amount of water must be reduced to not more than 5,000 ppm (mass) based on the urethane (meth)acrylate monomer without fail. This can be attained by contacting the second solution to a dehydrating agent (a treatment for contacting the second solution to the dehydrating agent may be simply referred to as "dehydration treatment" hereinafter). This dehydration treatment is preferably carried out until the amount of water becomes preferably not more than 3,000 ppm (mass), more preferably not more than 2,000 ppm (mass) based on the urethane (meth)acrylate monomer in order to suppress the production of the high-molecular weight impurity more efficiently. Although the lower limit of the amount of water is most preferably 0 ppm (mass, the detection limit of the measurement of the amount of water shown below) based on the urethane (meth)) acrylate monomer, it is 100 ppm (mass) in consideration of industrial-scale production.

This dehydration treatment must be carried out before the organic solvent is removed from the second solution. The second solution contains preferably 100 to 1,000 parts by mass, more preferably 100 to 500 parts by mass of the organic solvent based on 100 parts by mass of the urethane (meth)acrylate monomer. When the second solution contains the organic solvent within this range, the process can be simplified and the production of the high-molecular weight impurity can be suppressed more. The above preferred range of the amount of the organic solvent contained in the second solution does not differ from the preferred range of the amount of the organic solvent contained in the first solution based on the raw material urethane monomer. This is because the amount of the organic solvent based on the urethane (meth)acrylate monomer is not greatly changed by the reduction of the acid value and filtration.

As described above, the dehydration treatment must be carried out before the organic solvent is removed from the second solution. A description is subsequently given of the dehydrating agent.

Dehydrating Agent

In the present invention, the dehydrating agent is selected from inorganic salts, inorganic oxides, anhydrides thereof, partially dehydrated products and inorganic hydroxides. Specific examples thereof include inorganic salts such as magnesium sulfate, sodium sulfate, calcium sulfate, copper sulfate and calcium chloride, preferably anhydrides thereof; hydroxides such as calcium hydroxide; crystalline zeolite such as molecular sieves, and silica gel. Out of these dehydrating agents, anhydrides of an inorganic salt and crystalline zeolite are preferred, and anhydrous magnesium sulfate, anhydrous sodium sulfate, anhydrous calcium sulfate and molecular sieves are particularly preferred. These dehydrating agents may be used alone or in combination of two or more.

The amount of the dehydrating agent is such that the amount of water falls within the above range, preferably 0.1 to 50 parts by mass, more preferably 1 to 30 parts by mass based on 100 parts by mass of the urethane (meth)acrylate monomer.

Contact between the dehydrating agent and the second solution may be carried out by a known method. Preferably, the both are mixed together and stirred. The temperature for the dehydration treatment is not particularly limited but preferably 0 to 50° C. in order to suppress the production of the high-molecular weight impurity more. The treatment time is not particularly limited but may be determined by collecting part of the treated solution (third solution) and confirming that the amount of water becomes not more than 5,000 ppm (mass) based on the urethane (meth)acrylate monomer. It is generally 1 to 24 hours.

To remove the dehydrating agent after the treatment, a known method may be employed, and the dehydrating agent can be removed from the solution by filtration or centrifugation.

In the present invention, the amount of water contained in the second solution can be reduced to not more than 5,000 ppm (mass) based on the urethane (meth)acrylate monomer by the above method. A urethane (meth)acrylate monomer having high purity can be produced by removing the organic solvent from the obtained solution (third solution).

A description is subsequently given of the step (3) of removing the organic solvent from the third solution.

<Step (3) of Removing Organic Solvent>

The third solution obtained in the above step (2) contains the organic solvent, the urethane (meth)acrylate monomer having an acid value of not more than 0.2 mgKOH/g and not more than 5,000 ppm (mass) of water based on the urethane (meth)acrylate monomer as described above. In this third solution, the amount of the organic solvent preferably falls within the same range as that of the organic solvent contained in the first solution and the second solution. That is, the third solution contains the organic solvent in an amount of preferably 100 to 1,000 parts by mass, more preferably 100 to 500 parts by mass based on 100 parts by mass of the urethane (meth)acrylate monomer. A urethane (meth)acrylate monomer having a reduced acid value, a low content of a hardly soluble high-molecular weight impurity which is crosslinked high-dimensionally, a small amount of water and high purity can be produced more efficiently by removing the organic solvent from the third solution having a water content of not more than 5,000 ppm (mass) and an organic solvent content within the above range.

The method of removing the organic solvent from the third solution is not particularly limited, and the organic solvent may be removed by distillation. However, since the amount of the high-molecular weight impurity may increase when the third solution is treated at a high temperature, the temperature is preferably in the range of 30 to 70° C. Therefore, distillation under reduced pressure is preferably carried out to ensure that the temperature falls within the above range.

According to the above process, a urethane (meth)acrylate monomer having high purity can be produced.

<High-Purity Urethane (Meth) Acrylate Monomer>

According to the above process, there can be obtained a urethane (meth)acrylate monomer having a water content of not more than 2,000 ppm (mass), an acid value of not more than 0.2 mgKOH/g and preferably a content of the hardly soluble high-molecular weight component which has a number average molecular weight of not less than 5,000 and is crosslinked high-dimensionally of less than 0.3 mass %. The content of the high-molecular weight component in the obtained urethane (meth) acrylate monomer can be reduced to 0.0 mass % (detection limit measured by the following method) by adjusting production conditions. The lower limit of the water content is 100 ppm (mass) in consideration of industrial-scale production.

The urethane (meth) acrylate monomer obtained by the process of the present invention has a urethane bond and a (meth) acryloyl group in the molecule and is synthesized from a combination of a polyisocyanate and a hydroxyalkyl (meth) acrylate and optionally a polyol compound.

<Cured Product, Production Process Thereof, Polymerization Initiator>

A cured product can be obtained by using the high-purity urethane (meth) acrylate monomer obtained by the present invention. In this case, the high-purity urethane (meth) acrylate monomer may be used as a single component but it may be mixed with another polymerizable monomer to be used as a monomer composition. Although a monomer copolymerizable with the urethane (meth)acrylate monomer may be used as the polymerizable monomer constituting the monomer composition without restriction, a monovalent or polyvalent acrylate compound or methacrylate compound, a polyallyl compound and a polythioacrylate or polythiomethacrylate compound may be preferably used.

The mixing ratio of the urethane (meth)acrylate monomer and the monomer copolymerizable with the above monomer may be determined according to purpose. The copolymerizable monomer may be used in an amount of preferably 20 to 20,000 parts by mass, more preferably 50 to 15,000 parts by mass, particularly preferably 100 to 10,000 parts by mass based on 100 parts by mass of the urethane (meth)acrylate monomer.

The copolymerizable monomer may be suitably determined according to use purpose. Specific examples thereof include polyacrylate and polymethacrylate compounds such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl)propane and 2,2-bis(3,5-dibromo-4-methacryloyloxyethoxyphenyl) propane; polyallyl compounds such as diallyl phthalate, diallyl terephthalate, diallyl isophthalate, diallyl tartarate, diallyl epoxysuccinate, diallyl fumarate, diallyl chiorendate, diallyl hexaphthalate, diallyl carbonate, allyl diglycol carbonate and trimethylolpropane triallyl carbonate; polythioacrylate and polythiomethacrylate compounds such as 1,2-bis(methacryloylthio)ethane, bis(2-acryloylthioethyl)ether and 1,4-bis(methacryloylthiomethyl)benzene; acrylate compounds and methacrylate compounds such as glycidyl acrylate, glycidyl methacrylate, β-methyl glycidyl methacrylate, bisphenol A-monoglycidyl ether-methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate and 3-glycidyloxy-2-hydroxypropyloxy)-2-hydroxypropyl acrylate; and monomers such as divinyl benzene.

When the above cured product is used for application in photochromic plastic lenses, a copolymerizable monomer such as polyethylene glycol diacrylate, glycidyl methacrylate, bisphenol A dimethacrylate, 2,2-bis(4-methacryloyloxypentaethoxyphenyl)propane or trimethylolpropane trimethacrylate is preferably used.

An optical material which has excellent mechanical strength, low shrinkage, high storage stability and high weather resistance can be obtained by combining one of these copolymerizable monomers and the high-purity urethane (meth)acrylate monomer of the present invention. A photochromic composition may be obtained by mixing the monomer composition with a photochromic compound.

Although the ratio of the total of polymerizable monomer components which are the high-purity urethane (meth)acrylate monomer and the monomer copolymerizable with the above monomer to the photochromic compound is not particularly limited in the above photochromic composition, the photochromic compound is used in an amount of preferably 0.01 to 30 parts by mass, more preferably 0.01 to 10 parts by mass based on 100 parts by mass of the total of the polymerizable monomer components.

The method of curing the photochromic composition of the present invention is not particularly limited, the photochromic composition can be cured with heat and/or light, and a polymerization initiator may be optionally used.

The polymerization initiator used for thermal curing is not particularly limited, and examples thereof include diacyl peroxides such as benzoyl peroxide, p-chlorobenzoyl peroxide, decanoyl peroxide, lauroyl peroxide and acetyl peroxide; peroxy esters such as t-butylperoxy-2-ethyl hexanoate, t-butylperoxy dicarbonate, cumylperoxy neodecanate, t-butylperoxy benzoate and t-butylperoxy isobutyrate; percarbonates such as diisopropyl peroxydicarbonate, di-2-ethylhexyl peroxydicabonate and di-sec-butyloxy carbonate; and azo compounds such as 2,2'-azobisisobutyronitrile, 2,2'-azobis(4-dimethylvaleronitrile), 2,2'-azobis(2-methylbutyronitrile) and 1,1'-azobis(cyclohexane-1-carbonitrile).

The polymerization initiator which is used for optical curing is not particularly limited, and examples thereof include benzoin, benzoin methyl ether, benzoin butyl ether, benzophenol, acetophenone, 4,4'-dichlorobenzophenone, diethoxyacetophenone, 2-hydroxy-2-methyl-1-phenylpropan-1-one, benzyl methyl ketal, 1-(4-isopropylphenyl)-2-hydroxy-2-methylpropan-1-one, 1-hydroxycyclohexylphenyl ketone, 2-isopropylthioxanthone, bis(2,4,6-trimethylbenzoyl)phenylphosphine oxide and bis(2,6-dimethoxybenzoyl)-2,4,4-trimethylpentylphosphine oxide.

<Photochromic Compound>

As the photochromic compound in use, known photochromic compounds such as chromene compounds, fulgimide compounds, spirooxazine compounds, spiropyran compounds and bisimidazole compounds may be used without restriction. They may be used alone or in combination of two or more.

The above fulgimide compounds, spirooxazine compound, spiropyran compounds and chromene compounds include compounds disclosed by JP-A 2-28154, JP-A 62-288830, WO94/22850 and WO96/14596.

There are known chromene compounds having excellent photochromic properties besides those described in the above patent documents and may be preferably used as the component B. These chromene compounds are disclosed by JP-A 2001-031670, JP-A 2001-011067, JP-A 2001-011066, JP-A 2000-344761, JP-A 2000-327675, JP-A 2000-256347, JP-A 2000-229976, JP-A 2000-229975, JP-A 2000-229974, JP-A 2000-229973, JP-A 2000-229972, JP-A 2000-219678, JP-A 2000-219686, JP-A 11-322739, JP-A 11-286484, JP-A 11-279171, JP-A 09-218301, JP-A 09-124645, JP-A 08-295690, JP-A 08-176139, JP-A 08-157467, U.S. Pat. No. 5,645,767, U.S. Pat. No. 5,658,501, U.S. Pat. No. 5,961,892, U.S. Pat. No. 6,296,785, Japanese Patent No. 4424981, Japanese Patent No. 4424962, WO2009/136668, WO2008/023828, Japanese Patent No. 4369754, Japanese Patent No. 4301621, Japanese Patent No. 4256985, WO2007/086532, JP-A 2009-120536, JP-A 2009-67754, JP-A 2009-67680, JP-A 2009-57300, Japanese Patent No. 4195615, Japanese Patent No. 4158881, Japanese Patent No. 4157245, Japanese Patent No. 4157239, Japanese Patent No. 4157227, Japanese Patent No. 4118458, JP-A 2008-74832, Japanese Patent No. 3982770, Japanese Patent No. 3801386, WO2005/028465, WO2003/042203, JP-A 2005-289812, JP-A 2005-289807, JP-A 2005-112772, Japanese Patent No. 3522189, WO2002/090342, Japanese Patent No. 3471073, JP-A 2003-277381, WO2001/060811 and WO00/71544.

Since chromene-based photochromic compounds out of these photochromic compounds have higher durability of photochromic properties than other photochromic compounds and greater improvement of color optical density and fading speed out of photochromic properties by the present invention than other photochromic compounds, they can be particularly preferably used.

At least one of the photochromic compounds used in the present invention is preferably a chromene-based compound, particular preferably an indenonaphthopyran compound represented by the following formula out of the chromene-based compounds.

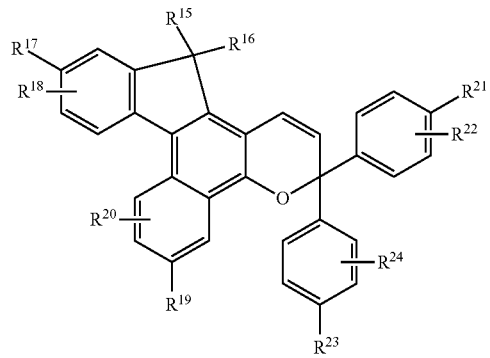

(In the above formula, $R^{15}$ to $R^{24}$ are each independently a hydrogen atom, hydroxyl group, alkyl group, cycloalkyl group, alkoxy group, aralkyl group, aralkoxy group, aryl group, substituted amino group having an alkyl group or an aryl group as a substituent, heterocyclic group having a nitrogen atom as a hetero atom and bonded via the nitrogen atom, cyano group, nitro group, halogen atom, halogenoalkyl group, halogenoalkoxy group, thioalkyl group or thioaryl group, and $R^{15}$ and $R^{16}$ may be bonded together to from a ring.)

The alkyl group is not particularly limited but preferably an alkyl group having 1 to 9 carbon atoms. Preferred examples thereof include methyl group, ethyl group, propyl group and butyl group.

The cycloalkyl group is not particularly limited but preferably a cycloalkyl group having 3 to 12 carbon atoms. Preferred examples of the cycloalkyl group include cyclopropyl group, cyclobutyl group, cyclopentyl group, cyclohexyl group, cycloheptyl group and cyclooctyl group.

The alkoxy group is not particularly limited but preferably an alkoxy group having 1 to 5 carbon atoms. Preferred examples of the alkoxy group include methoxy group, ethoxy group, propoxy group and butoxy group.

The aralkyl group is not particularly limited but preferably an aralkyl group having 7 to 11 carbon atoms. Preferred examples of the aralkyl group include benzyl group, phenylethyl group, phenylpropyl group and phenylbutyl group.

The aralkoxy group is not particularly limited but preferably an aralkoxy group having 6 to 10 carbon atoms. Preferred examples of the aralkoxy group include phenoxy group and naphthoxy group.

The aryl group is not particularly limited but preferably an aromatic hydrocarbon group having 6 to 10 carbon atoms or an aromatic heterocyclic group having 4 to 12 atoms forming a ring. Preferred examples of the aryl group include phenyl group, naphthyl group, thienyl group, furyl group, pyrrolinyl group, pyridyl group, benzothienyl group, benzofuranyl group and benzopyrrolinyl group. Substituted aryl groups obtained by substituting one or more hydrogen atoms of the aryl group by a substituent such as the same alkyl group or alkoxy group as above, a substituted amino group having an alkyl group or an aryl group which is described below, or a heterocyclic group having a nitrogen atom as a hetero atom and bonded via the nitrogen atom may also be preferably used.

The substituted amino group having an alkyl group or an aryl group as a substituent is preferably selected from alkylamino group, dialkylamino group, arylamino group and diarylamino group, and examples thereof include methylamino group, ethylamino group, phenylamino group, dimethylamino group, diethylamino group and diphenylamino group.

The heterocyclic group has a nitrogen atom as a hetero atom and is bonded via the nitrogen atom, and examples thereof include morpholino group, thiomorpholino group, piperidino group, pyrrolidinyl group, piperazino group, N-methylpiperazino group and indolinyl group.

Examples of the halogen atom are fluorine atom, chlorine atom, bromine atom and iodine atom.

The halogenoalkyl group is obtained by substituting one or more hydrogen atoms of the above alkyl group by a fluorine atom, chlorine atom or bromine atom. A halogenoalkyl group substituted by a fluorine atom out of these is preferred. Preferred examples of the halogenoalkyl group include fluoromethyl group, difluoromethyl group and trifluoromethyl group.

The halogenoalkoxy group is obtained by substituting one or more hydrogen atoms of the above alkoxy group by a fluorine atom, chlorine atom or bromine atom. A halogenoalkoxy group substituted by a fluorine atom out of these is preferred. Preferred examples of the halogenoalkoxy group include fluoromethoxy group, difluoromethoxy group and trifluoromethoxy group.

The thioalkyl group is obtained by substituting the oxygen atom of the above alkoxy group by a sulfur atom. Preferred examples thereof include thiomethyl group, thioethyl group and thiopropoxy group.

The thioaryl group is obtained by substituting the oxygen atom of the above aralkoxy group by a sulfur atom. Preferred examples thereof include thiophenyl group and thionaphthyl group.

The ring formed by bonding $R^{15}$ and $R^{16}$ together is preferably an aliphatic hydrocarbon ring having 4 to 10 carbon atoms. An aromatic hydrocarbon ring such as benzene, naphthalene, phenanthrene or anthracene may be condensed to the aliphatic hydrocarbon ring. The aliphatic hydrocarbon ring may have an alkyl group or alkoxy group having 1 to 5 carbon atoms as a substituent. Particularly preferred rings are given below. In the rings shown below, the carbon atom (spiro carbon atom) having two bonds at the lowest position corresponds to a carbon atom in a five-membered ring bonded to $R^{15}$ and $R^{16}$.

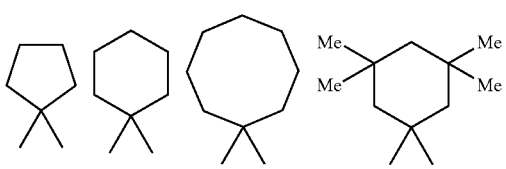

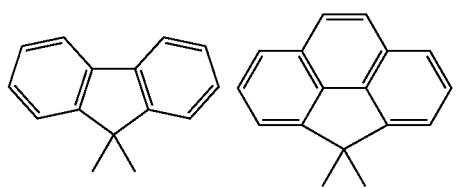

Preferred examples of the indenonaphthopyran compound used in the present invention are compounds represented by the following structures.

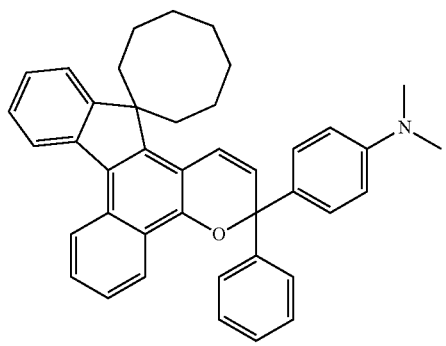

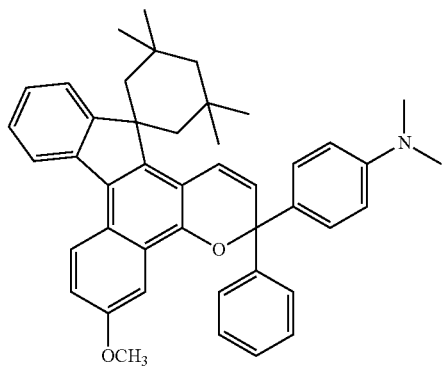

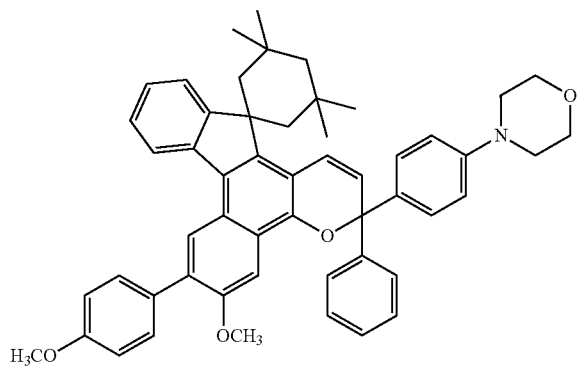

-continued

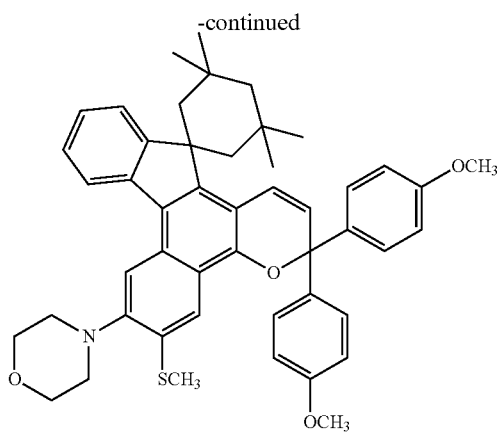

EXAMPLES

The following examples are provided for the purpose of further illustrating the present invention but are in no way to be taken as limiting.

Method of Determining the Amount of Acid Component:

The following titration was carried out to determine the amount of the acid component contained in the urethane (meth)acrylate monomer to evaluate the acid value.

An N/10 potassium hydroxide alcohol solution (ethanol solution (to be referred to as "measurement solution" hereinafter)) was set in a 2-ml micro-buret, and a stirrer was prepared. A graduated measuring cylinder was used to weigh 50 ml of ethanol and 50 ml of toluene accurately, and they were put into a 200-ml beaker and stirred and mixed together by means of the stirrer. 3 drops of a phenol phthalein solution were added to carry out empty titration with a volumetric solution. 20 g of a sample was added to the above solution after empty titration and stirred and mixed with the solution by means of the stirrer. Further, 3 drops of the phenol phthalein solution were added to carry out sample titration with a volumetric solution to obtain a titer. The method of calculating the acid value is based on the following equation.

Acid value (mgKOH/g)=titer (ml)×$f$ of volumetric solution×5.6 amount of sample (g)

In the above equation, f represents the factor of the volumetric solution obtained by using a standard hydrochloric acid solution. f of the N/10 potassium hydroxide alcohol solution used in the above method was 0.094. The amount of the sample is the weight of the urethane (meth)acrylate monomer contained in the sample.

Evaluation of Stability at the Time of Concentration of Solvent:

For the evaluation of stability at the time of the concentration of a solvent, the existence of the precipitation of a solid and a rise in viscosity was checked. The existence of the precipitation of a solid on the wall of a vessel used to concentrate the solvent and in the purified urethane (meth)acrylate monomer was checked visually. As for the existence of a rise in viscosity, the viscosity was measured by using a Cannon-Fenske viscometer, and changes in viscosity before and after purification were compared and evaluated.

Evaluation of High-Molecular Weight Impurity:

The evaluation of a high-molecular weight impurity was carried out by measuring the weight of a solid which is hardly soluble in tetrahydrofuran and the measurement of a tetrahydrofuran solution by gel permeation chromatography (GPC). The measurement conditions are as follows.

Measurement of Weight of Solid

A 1 mass % tetrahydrofuran solution of the purified urethane (meth)acrylate monomer was prepared, and the weight of insoluble matter separated by filtration with the quantitative filter paper (PTFE, 0.5 μm) of ADVANTEC Co., Ltd. was measured to calculate the weight ratio of the insoluble matter to the purified urethane (meth)acrylate monomer.

Measurement by Gel Permeation Chromatography (GPC)

Solid phase: KF8025 of Showa Denko K.K. (exclusion limit of 20,000)

Column oven temperature: 40° C.

Moving phase: tetrahydrofuran

Flow rate: 1 ml/min

Detector: $R^1$ detector 2414 of Waters Co., Ltd.

Calibration curve: standard polystyrene

The filtrate of the above tetrahydrofuran solution was measured by using the above equipment under the above conditions. In the present invention, the high-molecular weight component (high-molecular weight impurity) means the total of high-molecular weight components having an average molecular weight measured by the above method which is 3 times or more that of the urethane (meth)acrylate monomer, and the area % of the high-molecular weight component based on the area % of the urethane (meth) acrylate monomer is taken as the content (mass) of the high-molecular weight component.

Measurement of Amount of Water

The amount of water contained in the monomer was measured by a Karl Fischer method using the Karl Fischer aquameter (product name: MKA-210) of Kyoto Electronics Manufacturing Co., Ltd. The Aquamicron of Mitsubishi Chemical Co., Ltd. was used as a titrant, and dehydrated methanol was used as a solvent.

Measurement of Shrinkage Factor:

The shrinkage factor of the urethane (meth)acrylate monomer was calculated from the following equation by obtaining the specific gravity $\rho_M$ (g/cm$^3$) of the monomer and the specific gravity $\rho_P$ (g/cm$^3$) of a cured product of the monomer.

Shrinkage factor (%)=(1−$\rho_M$/$\rho_P$)×100

The cured product of the urethane (meth)acrylate monomer was manufactured by a method which will be described hereafter, and the specific gravities of the monomer and the cured product were measured by a method using an aerometer or a picnometer (JIS K2249).

Cured Product and Production Process Thereof:

A polymerizable monomer composition containing a radical polymerization initiator was injected into a casting mold composed of a glass plate and a gasket made of an ethylene-vinyl acetate copolymer to carry out cast polymerization so as to manufacture a cured product. Polymerization was carried out in an air furnace by gradually raising the temperature from 30° C. to 90° C. over 18 hours and maintaining the temperature at 90° C. for 2 hours. After the end of polymerization, a polymer was taken out from the glass casting mold to obtain a cured product.

Photopolymerized Laminate and Production Process Thereof:

A polymerizable monomer composition containing a photopolymerization initiator was applied to the surface of a substrate and irradiated with light with which the photopolymerization initiator could react in an inert gas atmosphere so as to obtain a cured product having a cured film on the surface of the substrate. CR39 (refractive index of 1.50) which is an allyl resin plastic lens was used as the substrate, and the polymerizable monomer composition was applied to the substrate by means of the 1H-DX2 spin coater of MIKASA Co., Ltd. A 150 mW/cm² metal halide lamp was used as a light source to irradiate the polymerizable monomer composition in a nitrogen gas atmosphere for 2 minutes so as to obtain the cured product.

Evaluation of Photochromic Properties and Weather Resistance:

A photochromic cured product was used as a sample, and a beam having an intensity of 2.4 mW/cm² at a wavelength of 365 nm and 24 μW/cm² at a wavelength of 245 nm on the surface of the laminate was applied from the L-2480 (300 W) SHL-100 xenon lamp of Hamamatsu Photonics K.K. to the sample through an aero mass filter (manufactured by Corning Co., Ltd.) at 23° C. for 120 seconds to develop color so as to measure the photochromic properties of the laminate.

1) Maximum absorption wavelength (λmax): This is the maximum absorption wavelength after color development obtained by means of the spectrophotometer (MCPD3000 instantaneous multi-channel photodetector) of Otsuka Electronics Co., Ltd. The maximum absorption wavelength is connected with color at the time of color development.

2) Color optical density [ε(120)-ε(0)]: This is the difference between absorbance {ε(120)} after 120 seconds of exposure at the above maximum absorption wavelength and ε(0) under no exposure at the above maximum absorption wavelength. It can be said that as this value becomes higher, the photochromic properties become better.

3) degree of deterioration (%)=[(1−A200/A0)×100]: The following deterioration promotion test was carried out to evaluate the weather resistance of a photochromic cured product by exposure. That is, the deterioration of the obtained photochromic cured product was promoted by using the ×25 xenon weather meter of Suga Test Instruments Co., Ltd. for 200 hours. Thereafter, the above color optical density was evaluated before and after the test, and the color optical density (A0) before the test and the color optical density (A200) after the test were measured to obtain a value of [(1−A200)/A0]×100] as the degree of deterioration (%) which is used as an index of the weather resistance of a photochromic cured product. As the degree of deterioration becomes lower, the weather resistance of the photochromic cured product becomes higher.

4) degree of coloration (ΔYI): The degree of coloration was measured by using the color difference meter (SM-4) of Suga Test Instruments Co., Ltd. A change in YI by the deterioration promotion test was designated as ΔYI which is used as an index of the degree of coloration caused by deterioration. It can be said that as the ΔYI value becomes smaller, the weather resistance of the cured product becomes higher.

Example 1

(1) Step (1) of Reducing Acid Component 1,000 g of a commercially available aliphatic urethane acrylate monomer having a structure represented by the following formula (acid value of 5.90 mgKOH/g, high-molecular weight impurity content of 0.1 mass %, 2 acryloyl functional groups, water content of 1,500 ppm (mass)) was dissolved in 3,500 g of toluene and stirred and dispersed completely (first solution).

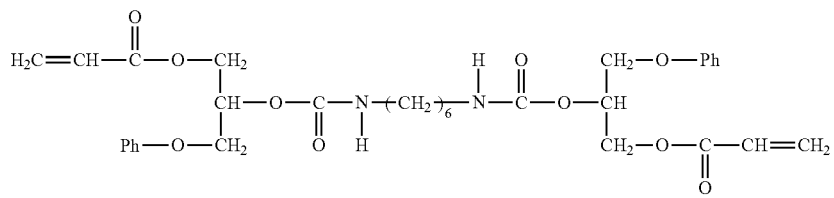

300 g of Kyoward 200 (Al(OH)$_3$.nH$_2$O (n=0.5 to 3), manufactured by Kyowa Chemical Industry Co., Ltd.) was added to the obtained first solution and stirred at 25° C. for 8 hours. After the end of agitation, Kyoward 200 was filtered with the quantitative filter paper (No. 2) of ADVANTEC Co., Ltd. using a Nutshe. The acid value of the urethane acrylate monomer contained in the obtained second solution was 0.10 mgKOH/g in terms of a monomer. This second solution contained 9,000 ppm (mass) of water based on the urethane acrylate monomer.

(2) Step (2) of Dehydration 100 g of crystalline zeolite (Molecular Sieve 4A (diameter of 1.6 mm, manufactured by Wako Pure Chemical Industries, Ltd.)) as a dehydrating agent was added to the above toluene solution of the urethane acrylate monomer (second solution) and stirred at 25° C. for 6 hours, and the obtained solution was filtered with the PTFE filter paper (0.5 μm) of ADVANTEC Co., Ltd. The obtained third solution contained 1,300 ppm (mass) of water based on the urethane acrylate monomer.

(3) Step (3) of Removing Organic Solvent

Then, to distill off toluene from the third solution, the distillation-off of the solvent was carried out under a reduced pressure of 10 mmHg at 50° C. for 8 hours to obtain a purified urethane acrylate monomer. The amount of the residual toluene was 0.2 mass %. The precipitation of a solid was not seen on the wall of a reactor used for the distillation-off of the solvent and in the purified urethane acrylate monomer, and a rise in viscosity was not observed. When the weight measurement and GPC measurement of an insoluble component were made on a 1 mass % tetrahydrofuran solution of the purified urethane acrylate monomer, no high-molecular weight impurity was seen. The amount of water was 600 ppm (mass) and the acid value was 0.08 mgKOH/g. The shrinkage factor of the purified urethane acrylate monomer was 6.2%.

Example 2

(1) Step (1) of Reducing Acid Component 1,000 g of a commercially available aliphatic urethane acrylate monomer having a structure represented by the following formula (acid value of 0.95 mgKOH/g, high-molecular weight impurity content of 0.0 mass %, 2 acryloyl functional groups, water content of 900 ppm (mass)) was dissolved in 2,500 g of toluene and stirred and dispersed completely (first solution).

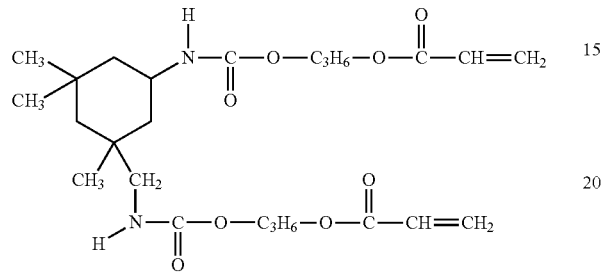

250 g of Kyoward 200 (of Kyowa Chemical Industry Co., Ltd.) was added to the obtained first solution and stirred at 25° C. for 8 hours. After the end of agitation, Kyoward 200 was filtered with the quantitative filter paper (No. 2) of ADVANTEC Co., Ltd. using a Nutshe. The acid value of the urethane acrylate monomer contained in the obtained second solution was 0.03 mgKOH/g in terms of a monomer. This second solution contained 8,000 ppm (mass) of water based on the urethane acrylate monomer.

(2) Step (2) of Dehydration 100 g of crystalline zeolite (Molecular Sieve 4A (diameter of 1.6 mm, manufactured by Wako Pure Chemical Industries, Ltd.)) as a dehydrating agent was added to the above toluene solution of the urethane acrylate monomer (second solution) and stirred at 25° C. for 6 hours, and the obtained solution was filtered with the PTFE filter paper (0.5 μm) of ADVANTEC Co., Ltd. The obtained third solution contained 1,200 ppm (mass) of water based on the urethane acrylate monomer.

(3) Step (3) of Removing Organic Solvent

Then, to distill off toluene from the third solution, the distillation-off of the solvent was carried out under a reduced pressure of 10 mmHg at 50° C. for 8 hours to obtain a purified urethane acrylate monomer. The amount of the residual toluene was 0.4 mass %. The precipitation of a solid was not seen on the wall of a reactor used for the distillation-off of the solvent and in the purified urethane acrylate monomer, and a rise in viscosity was not observed. When the weight measurement and GPC measurement of an insoluble component were made on a 1 mass % tetrahydrofuran solution of the purified urethane acrylate monomer, no high-molecular weight impurity was seen. The amount of water was 400 ppm (mass) and the acid value was 0.03 mgKOH/g. The shrinkage factor of the purified urethane acrylate monomer was 8.4%.

Example 3

(1) Step (1) of Reducing Acid Component 1,000 g of an aliphatic urethane acrylate monomer having a structure represented by the following formula and obtained by reacting hexamethylene-1,6-diisocyanate with 2-hydroxypropyl acrylate (acid value of 0.91 mgKOH/g, high-molecular weight impurity content of 0.0 mass %, 2 acryloyl functional groups, water content of 1,200 ppm (mass)) was dissolved in 3,000 g of ethyl acetate and stirred and dispersed completely (first solution).

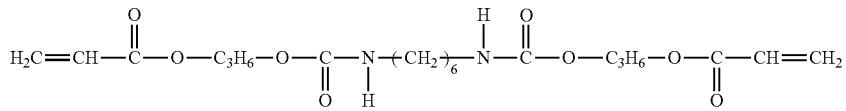

200 g of Kyoward 200 (of Kyowa Chemical Industry Co., Ltd.) was added to the obtained first solution and stirred at 25° C. for 8 hours. After the end of agitation, Kyoward 200 was filtered with the quantitative filter paper (No. 2) of ADVANTEC Co., Ltd. using a Nutshe. The acid value of the urethane acrylate monomer contained in the obtained second solution was 0.04 mgKOH/g in terms of a monomer. This second solution contained 9,000 ppm of water based on the urethane acrylate monomer.

(2) Step (2) of Dehydration 100 g of crystalline zeolite (Molecular Sieve 4A (diameter of 1.6 mm, manufactured by Wako Pure Chemical Industries, Ltd.)) as a dehydrating agent was added to the above ethyl acetate solution of the urethane acrylate monomer (second solution) and stirred at 25° C. for 6 hours, and the obtained solution was filtered with the PTFE filter paper (0.5 μm) of ADVANTEC Co., Ltd. The obtained third solution contained 1,900 ppm of water based on the mass of the urethane methacrylate monomer.

(3) Step (3) of Removing Organic Solvent

Then, to distill off ethyl acetate from the third solution, the distillation-off of the solvent was carried out under a reduced pressure of 10 mmHg at 50° C. for 8 hours to obtain a purified urethane acrylate monomer. The amount of the residual ethyl acetate was 0.1 mass %. The precipitation of a solid was not seen on the wall of a reactor used for the distillation-off of the solvent and in the purified urethane acrylate monomer, and a rise in viscosity was not observed. When the weight measurement and GPC measurement of an insoluble component were made on a 1 mass % tetrahydrofuran solution of the purified urethane acrylate monomer, no high-molecular weight impurity was seen. The amount of water was 700 ppm (mass) and the acid value was 0.03 mgKOH/g. The shrinkage factor of the purified urethane acrylate monomer was 8.2%.

Comparative Example 1

For comparison, after the step of reducing the acid component was carried out in the same manner as in Example 1, the step of removing the organic solvent was carried out without carrying out the step of dehydration.

(1) Step (1) of Reducing Acid Component 1,000 g of the same aliphatic urethane acrylate monomer as in Example 1 (acid value of 5.90 mgKOH/g, high-molecular weight impurity content of 0.1 mass %, 2 acryloyl functional groups, water content of 1,500 ppm (mass)) was dissolved in 3,500 g of toluene and stirred and dispersed completely (first solution). 500 g of Kyoward 200 (of Kyowa Chemical Industry Co., Ltd.) was added to the obtained first solution and stirred at 25° C. for 8 hours. After the end of agitation, Kyoward 200 was filtered with the quantitative filter paper (No. 2) of ADVANTEC Co., Ltd. using a Nutshe. The acid value of the urethane acrylate monomer contained in the obtained second solution was 0.09 mgKOH/g in terms of a monomer. The second solution contained 11,000 ppm (mass) of water based on the urethane acrylate monomer.

(2) Step (3) of Removing Organic Solvent

Then, to distill off toluene from the above second solution, the distillation-off of the solvent was carried out under a reduced pressure of 10 mmHg at 50° C. for 8 hours to obtain a purified urethane acrylate monomer. The amount of the residual toluene was 0.4 mass %. The precipitation of a small amount of a white solid (insoluble matter) was seen on the wall of a reactor used for the distillation-off of the solvent, and the viscosity at 50° C. rose by 30%. When the weight measurement and GPC measurement of an insoluble component were made on a 1 mass % tetrahydrofuran solution of the purified urethane acrylate monomer, 1.2 mass % of the insoluble component was produced and 0.4 mass % of a high-molecular weight impurity having a molecular weight which was 3 times or more that of the urethane acrylate monomer was confirmed by GPC measurement. The amount of water was 1,200 ppm (mass) and the acid value was 0.09 mgKOH/g. The shrinkage factor of the purified urethane acrylate monomer was 6.2%.

Comparative Example 2

For comparison, commercially available activated carbon was used in place of the inorganic adsorbent in the step of reducing the acid component.

1,000 g of the same aliphatic urethane acrylate monomer as in Example 1 (acid value of 5.90 mgKOH/g, high-molecular weight impurity content of 0.1 mass %, 2 acryloyl functional groups, water content of 1,500 ppm (mass)) was dissolved in 3,500 g of toluene and stirred and dispersed completely (first solution). 50 g of activated carbon ("Purified Shirasagi" of Nippon Envirochemicals Co., Ltd.) was added to the obtained first solution and stirred at 25° C. for 8 hours. After the end of agitation, the obtained solution was filtered with the quantitative filter paper (No. 2) of ADVAN-TEC Co., Ltd. using a Nutshe to remove the activated carbon. The acid value of the urethane acrylate monomer contained in the obtained second solution was 5.41 mgKOH/g in terms of a monomer. Therefore, the effect of reducing the acid value was extremely low. Since the acid value could not be reduced fully, the subsequent steps were not carried out.

Comparative Example 3

(1) Step (1) of Reducing Acid Component 1,000 g of the same aliphatic urethane acrylate monomer as in Example 2 (acid value of 0.95 mgKOH/g, high-molecular weight impurity content of 0.0 mass %, 2 acryloyl functional groups, water content of 900 ppm (mass)) was dissolved in 3,000 g of ethanol and stirred and dispersed completely (first solution). 250 g of Kyoward 200 (of Kyowa Chemical Industry Co., Ltd.) was added to the obtained first solution and stirred at 25° C. for 8 hours. After the end of agitation, Kyoward 200 was filtered with the quantitative filter paper (No. 2) of ADVANTEC Co., Ltd. using a Nutshe. The acid value of the urethane acrylate monomer contained in the obtained second solution was 0.03 mgKOH/g in terms of a monomer. The second solution contained 31,000 ppm (mass) of water based on the urethane acrylate monomer.

(2) Step (3) of Removing Organic Solvent

Then, to distill off ethanol from the second solution, the distillation-off of the solvent was carried out under a reduced pressure of 10 mmHg at 50° C. for 8 hours to obtain a purified urethane acrylate monomer. The amount of the residual ethanol was 0.1 mass %. The precipitation of a small amount of a white solid (insoluble matter) was seen on the wall of a reactor used for the distillation-off of the solvent, and the viscosity at 50° C. rose by 20%. When the weight measurement and GPC measurement of an insoluble component were made on a 1 mass % tetrahydrofuran solution of the purified urethane acrylate monomer, 0.8 mass % of an insoluble component was produced and 0.4 mass % of a high-molecular weight impurity having a molecular weight which is 3 times or more that of the urethane acrylate monomer was confirmed by GPC measurement. The amount of water was 2,900 ppm (mass) and the acid value was 0.03 mgKOH/g. The shrinkage factor of the purified urethane acrylate monomer was 8.4%.
(there is no Example 4)

Example 5

Experiment on Comparison of Storage Stability

When the same aliphatic urethane acrylate monomer as in Example 2 (acid value of 0.95 mgKOH/g, high-molecular weight impurity content of 0.0 mass %, 2 acryloyl functional groups, water content of 900 ppm (mass)) was heated at 50° C. in a nitrogen atmosphere and stirred, a small amount of a solid was precipitated on the wall of an oven and the viscosity rose by 20% after 24 hours.

Meanwhile, when the same operation was carried out by using the purified urethane acrylate monomer obtained in Example 2, the precipitation of a solid was not seen and an increase in viscosity was not observed even after 96 hours.

It is understood from this result that the storage stability of urethane acrylate purified by the method of the present invention is high.

Example 6

(1) Step (1) of Reducing Acid Component 1,000 g of an aliphatic urethane acrylate monomer represented by the following structural formula and obtained by reacting isophorone diisocyanate with 2-hydroxyethyl acrylate (acid value of 1.21 mgKOH/g, high-molecular weight impurity content of 0.0 mass %, 2 acryloyl functional groups, molecular weight of 454, water content of 900 ppm (mass)) was dissolved in 3,500 g of toluene and stirred and dispersed completely (first solution).

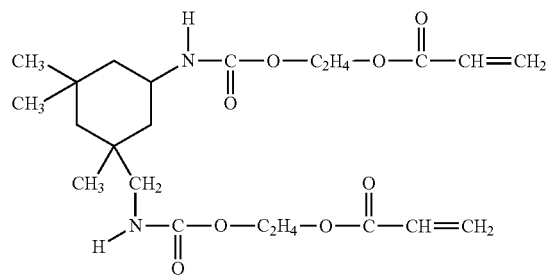

100 g of Kyoward 200 (of Kyowa Chemical Industry Co., Ltd.) was added to the obtained first solution and stirred at 25° C. for 8 hours. After the end of agitation, Kyoward 200 was filtered with the quantitative filter paper (No. 2) of ADVANTEC Co., Ltd.) using a Nutshe. The acid value of the urethane acrylate monomer contained in the obtained second solution was 0.02 mgKOH/g in terms of a monomer. The second solution contained 6,000 ppm of water based on the mass of the urethane acrylate monomer.

(2) Step (2) of Dehydration 100 g of crystalline zeolite (Molecular Sieve 4A (diameter of 1.6 mm, manufactured by Wako Pure Chemical Industries, Ltd.)) as a dehydrating agent was added to the above toluene solution of the urethane acrylate monomer (second solution) and stirred at 25° C. for 6 hours, and the obtained solution was filtered with the PTFE filter paper (0.5 μm) of ADVANTEC Co., Ltd. The obtained third solution contained 1,200 ppm of water based on the mass of the urethane acrylate monomer.

(3) Step (3) of Removing Organic Solvent

Then, to distill off toluene from the third solution, the distillation-off of the solvent was carried out under a reduced pressure of 10 mmHg at 50° C. for 8 hours to obtain a purified urethane acrylate monomer. The amount of the residual toluene was 0.6 mass %. The precipitation of a solid was not seen on the wall of a reactor used for the distillation-off of the solvent and in the purified urethane acrylate monomer, and a rise in viscosity was not observed. When the weight measurement and GPC measurement of an insoluble component were made on a 1 mass % tetrahydrofuran solution of the purified urethane (meth)acrylate monomer, no high-molecular weight impurity was seen. The amount of water was 400 ppm (mass) and the acid value was 0.02 mgKOH/g. The shrinkage factor of the purified urethane acrylate monomer was 8.5%.

Example 7

(1) Step (1) of Reducing Acid Component 1,000 g of an aliphatic urethane acrylate monomer represented by the following structural formula and obtained by reacting 2,2,4-trimethylhexamethylene-1,6-diisocyanate with 2-hydroxyethyl acrylate (acid value of 1.59 mgKOH/g, high-molecular weight impurity content of 0.0%, 2 acryloyl functional groups, molecular weight of 442, water content of 1,100 ppm (mass)) was dissolved in 2,500 g of toluene and stirred and dispersed completely (first solution).

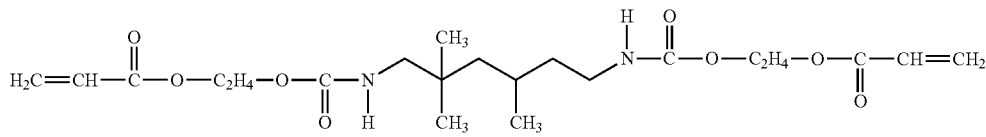

200 g of Kyoward 200 (of Kyowa Chemical Industry Co., Ltd.) was added to the obtained first solution and stirred at 25° C. for 8 hours. After the end of agitation, Kyoward 200 was filtered with the quantitative filter paper (No. 2) of ADVANTEC Co., Ltd.) using a Nutshe. The acid value of the urethane acrylate monomer contained in the obtained second solution was 0.05 mgKOH/g in terms of the monomer. This second solution contained 7,500 ppm of water based on the mass of the urethane acrylate monomer.

(2) Step (2) of Dehydration 100 g of crystalline zeolite (Molecular Sieve 4A (diameter of 1.6 mm, manufactured by Wako Pure Chemical Industries, Ltd.)) as a dehydrating agent was added to the above toluene solution of the urethane acrylate monomer (second solution) and stirred at 25° C. for 6 hours, and the obtained solution was filtered with the PTFE filter paper (0.5 μm) of ADVANTEC Co., Ltd. The obtained third solution contained 1,100 ppm of water based on the mass of the urethane acrylate monomer.

(3) Step (3) of Removing Organic Solvent

Then, to distill off toluene from the third solution, the distillation-off of the solvent was carried out under a reduced pressure of 10 mmHg at 50° C. for 8 hours to obtain a purified urethane acrylate monomer. The amount of the residual toluene was 0.2 mass %. The precipitation of a solid was not seen on the wall of a reactor used for the distillation-off of the solvent and in the purified urethane acrylate monomer, and a rise in viscosity was not observed. When the weight measurement and GPC measurement of an insoluble component were made on a 1 mass % tetrahydrofuran solution of the purified urethane acrylate monomer, no high-molecular weight impurity was seen. The amount of water was 400 ppm (mass) and the acid value was 0.05 mgKOH/g. The shrinkage factor of the purified urethane acrylate monomer was 9.1%.

Example 8

The steps (1) to (3) were carried out in the same manner as in Example 7 except that crystal water-containing Kyoward 300 ($2.5MgO \cdot Al_2O_3 \cdot nH_2O$ (n=0.5 to 3), manufactured by Kyowa Chemical Industry, Co., Ltd.) comprising aluminum oxide and magnesium oxide as the main components was used as an inorganic adsorbent. The results are shown in Table 1.

Example 9

The steps (1) to (3) were carried out in the same manner as in Example 7 except that crystal water-containing Kyoward 2000 ($Mg_{0.7}Al_{0.3}O_{1.15} \cdot nH_2O$ (n=0.1 to 2), manufactured by Kyowa Chemical Industry, Co., Ltd.) comprising magnesium oxide as the main component was used as an inorganic adsorbent. The results are shown in Table 1.

Example 10

The steps (1) to (3) were carried out in the same manner as in Example 7 except that crystal water-containing Tomix AD-200 ($Al_2O_3 \cdot nH_2O$ (n=0.5 to 3), manufactured by Tomita Pharmaceutical Co., Ltd.) comprising aluminum oxide as the main component was used as an inorganic adsorbent. The results are shown in Table 1.

Example 11

The steps (1) to (3) were carried out in the same manner as in Example 7 except that crystal water-containing Tomix AD-300 ($MgO \cdot Al_2O_3 \cdot 2SiO_2 \cdot nH_2O$ (n=0.5 to 3), manufactured by Tomita Pharmaceutical Co., Ltd.) comprising aluminum oxide and silicon dioxide as the main components was used as an inorganic adsorbent. The results are shown in Table 1.

TABLE 1

| | After step (1) | After step (2) | After step (3) | | | |
|---|---|---|---|---|---|---|
| | Acid value mg/KOH (g) | Amount of water ppm (mass) | Amount of water ppm (mass) | Amount of water ppm (mass) | Amount of high-molecular weight impurity % (mass) | Acid value mg/KOH (g) |
| Ex. 8 | 0.06 | 8000 | 1000 | 400 | N.D. | 0.06 |
| Ex. 9 | 0.09 | 5500 | 900 | 400 | N.D. | 0.09 |
| Ex. 10 | 0.13 | 9000 | 1200 | 500 | N.D. | 0.12 |
| Ex. 11 | 0.17 | 8000 | 1100 | 600 | N.D. | 0.17 |

Ex.: Example, N.D.: not detected

Example 12

The steps (1) to (3) were carried out in the same manner as in Example 7 except that a urethane acrylate monomer represented by the following structural formula and obtained by reacting isophorone diisocyanate, 2-hydroxyethyl acrylate and 1,6-hexamethylenediol (acid value of 2.4 mgKOH/g, high-molecular weight impurity content of 0.0%, 2 acryloyl functional groups, molecular weight of 795, water content of 1,200 ppm (mass)) was used and 300 parts by mass of toluene was used based on 100 parts by mass of the urethane acrylate monomer.

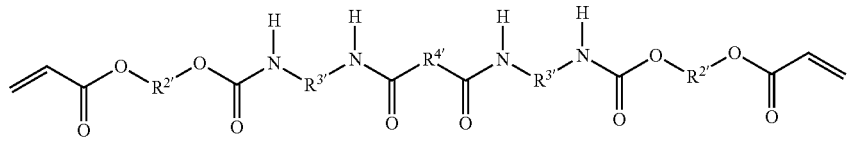

(In the above formula, $R^{2'}$ is $—C_2H_4—$, $R^{3'}$ is

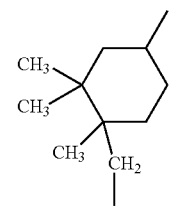

and $R^{4'}$ is $—OCH_2CH_2CH_2CH_2CH_2CH_2O—$.)

The results are shown in Table 2. The shrinkage factor of the purified urethane acrylate monomer was 6.1%

Example 13

The steps (1) to (3) were carried out in the same manner as in Example 7 except that a urethane acrylate monomer represented by the following structural formula and obtained by reacting 2,2,4-trimethylhexamethylene-1,6-diisocyanate, 2-hydroxypropyl acrylate and polyester polyol (acid value of 1.9 mgKOH/g, high-molecular weight impurity content of 0.0%, 2 acryloyl functional groups, molecular weight of about 1,100, water content of 800 ppm (mass)) was used and 250 parts by mass of toluene was used based on 100 parts by mass of the urethane acrylate monomer.

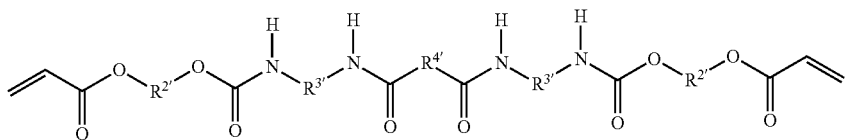

(In the above formula, $R^{2\prime}$ is —$C_3H_6$—, $R^{3\prime}$ is

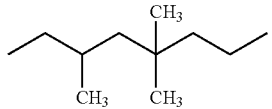

and $R^{4\prime}$ is

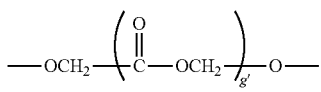

(in the formula, the average value of g's is 5.).)

The results are shown in Table 2. The shrinkage factor of the purified urethane acrylate monomer was 5.0%.

Example 14

The steps (1) to (3) were carried out in the same manner as in Example 7 except that a urethane acrylate monomer represented by the following structural formula and obtained by reacting isophorone diisocyanate, 2-hydroxyethyl acrylate and polycarbonate polyol (acid value of 4.1 mgKOH/g, high-molecular weight impurity content of 0.0%, 2 acryloyl functional groups, molecular weight of about 1,100, water content of 1,000 ppm (mass)) was used and 350 parts by mass of toluene was used based on 100 parts by mass of the urethane acrylate monomer.

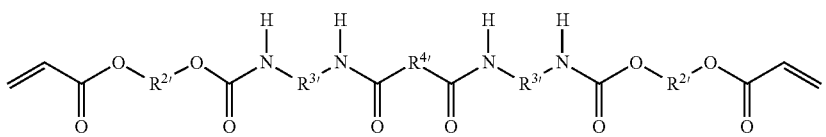

(In the above formula, $R^{2\prime}$ is —$C_2H_4$—, $R^{3\prime}$ is

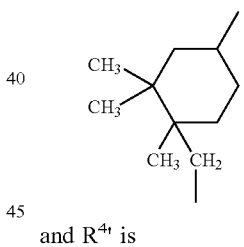

and $R^{4\prime}$ is

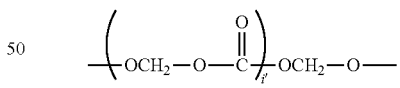

(in the formula, the average value of i's is 5.).)

The results are shown in Table 2. The shrinkage factor of the purified urethane acrylate monomer was 4.8%.

Example 15

The steps (1) to (3) were carried out in the same manner as in Example 7 except that a urethane acrylate monomer represented by the following structural formula and obtained by reacting isophorone diisocyanate with polycarbonate polyol and then reacting isophorone diamine with 2-hydroxyethyl acrylate (acid value of 3.6 mgKOH/g, high-molecular weight impurity content of 0.0%, 2 acryloyl functional groups, molecular weight of about 1,700, water content of 1,300 ppm (mass)) was used and 500 parts by mass of toluene was used based on 100 parts by mass of the urethane acrylate monomer.

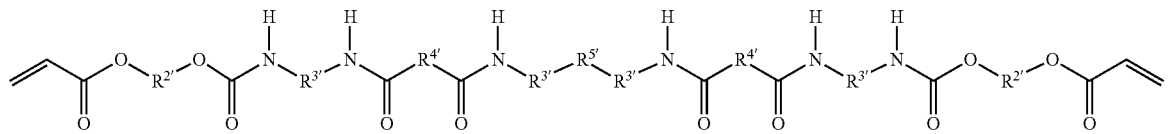

(In the above formula, $R^{2'}$ is —$C_2H_4$—, $R^{3'}$ is

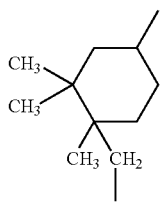

and $R^{4'}$ is

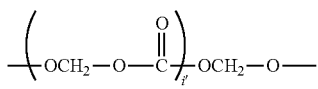

(in the above formula, the average value of i's is 5, and $R^{5'}$ is

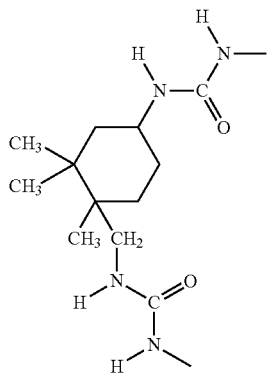

The results are shown in Table 2. The shrinkage factor of the purified urethane acrylate monomer was 2.9%.

Example 16

The steps (1) to (3) were carried out in the same manner as in Example 7 except that a urethane acrylate monomer represented by the following structural formula and obtained by reacting isophorone diisocyanate with polycarbonate polyol and then reacting 1,4-butanediol with 2-hydroxyethyl acrylate (acid value of 3.2 mgKOH/g, high-molecular weight impurity content of 0.0%, 2 acryloyl functional groups, molecular weight of about 1,600, water content of 1,400 ppm (mass)) was used and 500 parts by mass of toluene was used based on 100 parts by mass of the urethane acrylate monomer.

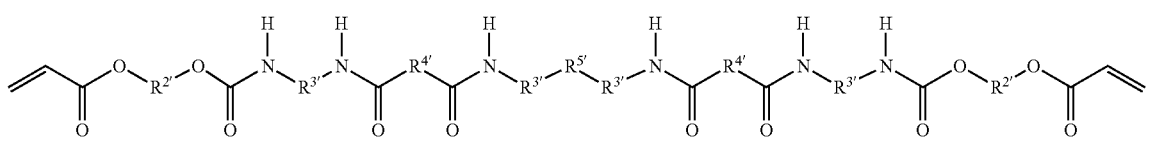

(In the above formula, $R^{2'}$, $R^{3'}$ and $R^{4'}$ are as defined in Example 15, and $R^{5'}$ is

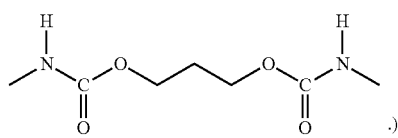

.)

The results are shown in Table 2. The shrinkage factor of the purified urethane acrylate monomer was 3.2%.

TABLE 2

| | After step (1) | After step (2) | After step (3) | | |
|---|---|---|---|---|---|
| | Acid value mg/KOH (g) | Amount of water ppm (mass) | Amount of water ppm (mass) | Amount of water ppm (mass) | high-molecular weight impurity % (mass) | Acid value mg/KOH (g) |
| Ex. 12 | 0.11 | 8500 | 1200 | 400 | N.D. | 0.11 |
| Ex. 13 | 0.08 | 8000 | 900 | 400 | N.D. | 0.08 |
| Ex. 14 | 0.14 | 9000 | 1100 | 500 | N.D. | 0.13 |
| Ex. 15 | 0.09 | 7500 | 1000 | 400 | N.D. | 0.09 |
| Ex. 16 | 0.12 | 7500 | 900 | 400 | N.D. | 0.11 |

Ex.: Example, N.D.: not detected

Example 17

Monomer Composition

A monomer composition was obtained by mixing together 17 parts by mass of the purified urethane acrylate monomer obtained in Example 14, 1 part by mass of glycidyl methacrylate, 6 parts by mass of trimethylolpropane trimethacrylate, 6 parts by mass of tetraethylene glycol diacrylate, 31 parts by mass of tetraethylene glycol dimethacrylate, 38 parts by mass of tetrapropylene glycol dimethacrylate and 1 part by mass of α-methyl styrene dimer completely under agitation as components of the monomer composition.

For comparison, a monomer composition comprising the same components as above was obtained except that an unpurified urethane acrylate monomer (acid value of 4.1 mgKOH/g) was used as a component of the above monomer composition.

When these monomer compositions were kept at 25° C. for 6 months to compare the colors of these monomers, it was confirmed that no change was seen in the monomer composition comprising the purified urethane acrylate monomer of Example 17 whereas the monomer composition comprising the unpurified urethane acrylate monomer was colored yellow.

Example 18

Monomer Composition

A monomer composition was obtained by mixing together 25 parts by mass of the purified urethane acrylate monomer obtained in Example 7, 1 part by mass of glycidyl methacrylate, 10 parts by mass of trimethylolpropane trimethacrylate, 41 parts by mass of tripropylene glycol dimethacrylate, 16 parts by mass of polyethylene glycol diacrylate (average molecular weight of ethylene glycol chain of 400), 5 parts by mass of methoxypolyethylene glycol methacrylate (average molecular weight of ethylene glycol chain of 400) and 2 parts by mass of α-methyl styrene dimer completely under agitation as components of the monomer composition.

For comparison, a monomer composition comprising the same components as above was obtained except that an unpurified urethane acrylate monomer (acid value of 1.59 mgKOH/g) was used as a component of the above monomer composition.

When these monomer compositions were kept at 25° C. for 6 months to compare the colors of these monomers, it was confirmed that no change was seen in the monomer composition comprising the purified urethane acrylate monomer of Example 18 whereas the monomer composition comprising the unpurified urethane acrylate monomer was colored yellow.

Example 19

Photochromic Composition, Cured Product 0.04 part by mass of a photochromic compound represented by the following structural formula (A) was added to 100 parts by mass of the monomer composition of Example 17 and fully mixed with the composition under agitation to obtain a photochromic composition.

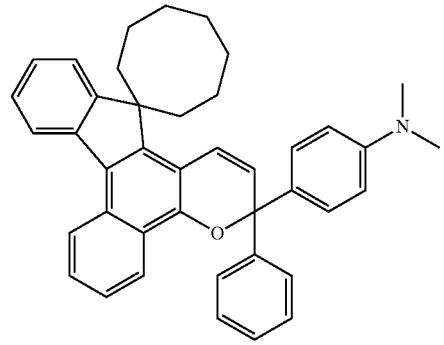

(A)

1 part of t-butylperoxy neodecanoate (Perbutyl ND of NOF Corporation) as a radical polymerization initiator was added to this photochromic composition to carry out cast polymerization so as to obtain a photochromic cured product. The photochromic properties and weather resistance of this photochromic cured product (thickness of 2 mm) were evaluated. The results are shown in Table 3.

Comparative Example 4

As comparison to Example 19, a photochromic composition and a photochromic cured product were obtained in the same manner as in Example 19 except that an unpurified urethane acrylate monomer (acid value of 4.1 mgKOH/g) was used. The evaluation results of photochromic properties and weather resistance are shown in Table 3.

TABLE 3

| | Maximum absorption wavelength | Color optical density | Degree of deterioration | Degree of coloration (ΔYI) |
|---|---|---|---|---|
| Ex. 19 | 576 nm | 0.68 | 8% | 2.8 |
| C. Ex. 4 | 576 nm | 0.69 | 17% | 4.2 |

Ex.: Example,
C. Ex.: Comparative Example

Example 20

A photochromic cured product was obtained in the same manner as in Example 19 except that 0.03 part by mass of a photochromic compound represented by the following structural formula (A), 0.01 part by mass of a photochromic compound represented by the following structural formula (B) and 0.015 part by mass of a photochromic compound represented by the following structural formula (C) were used based on 100 parts by mass of the monomer composition of Example 18. The evaluation results of photochromic properties and weather resistance are shown in Table 4.

Example 21

A photochromic cured product was obtained in the same manner as in Example 19 except that 0.05 part by mass of a photochromic compound represented by the following structural formula (D) and 0.02 part by mass of a photochromic compound represented by the following structural formula (B) were used based on 100 parts by mass of the monomer composition of Example 18. The evaluation results of photochromic properties and weather resistance are shown in Table 5.

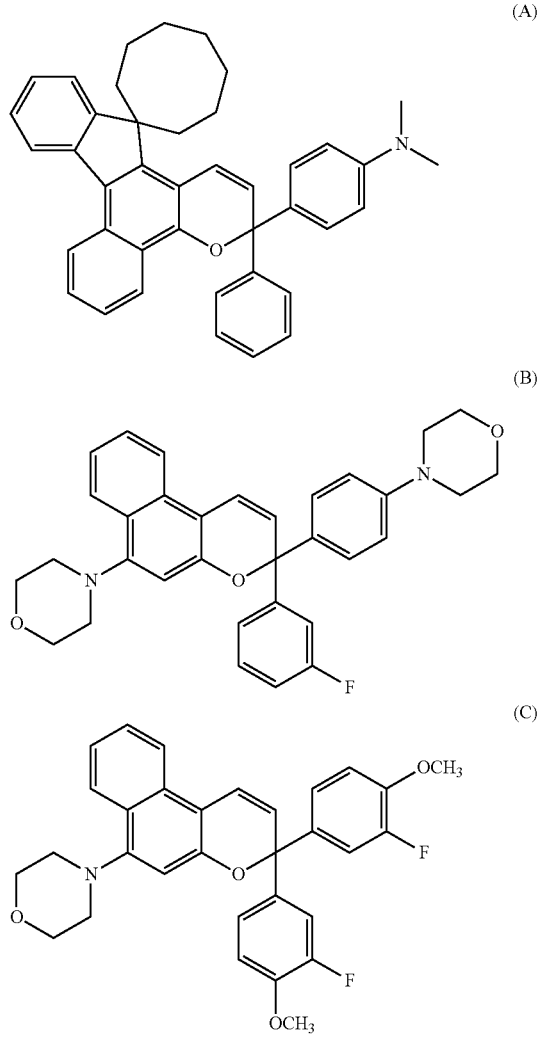

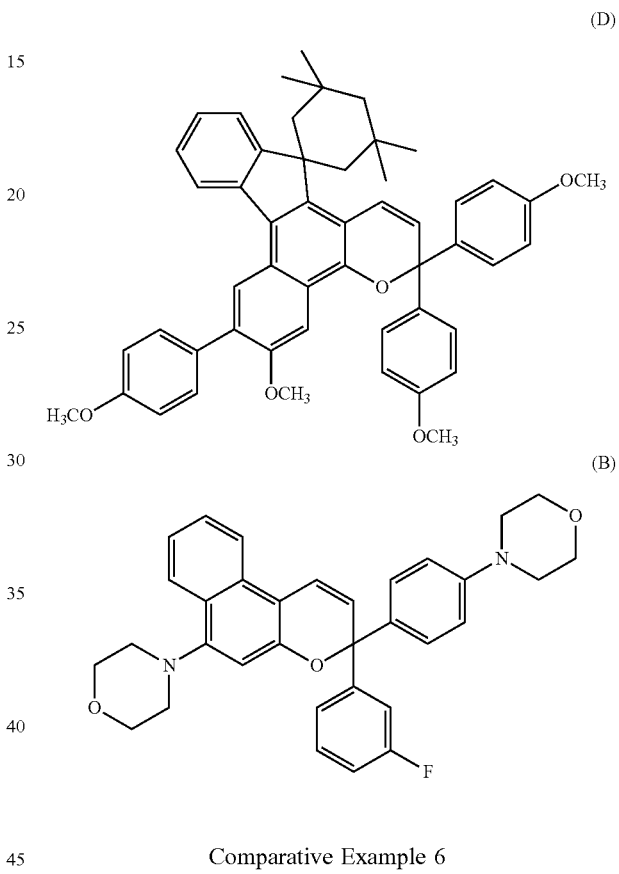

Comparative Example 5

As comparison to Example 20, a photochromic composition and a photochromic cured product were obtained in the same manner as in Example 20 except that an unpurified urethane acrylate monomer (acid value of 1.59 mgKOH/g) was used. The evaluation results of photochromic properties and weather resistance are shown in Table 4.

Comparative Example 6

As comparison to Example 21, a photochromic composition and a photochromic cured product were obtained in the same manner as in Example 21 except that an unpurified urethane acrylate monomer (acid value of 1.59 mgKOH/g) was used. The evaluation results of photochromic properties and weather resistance are shown in Table 5.

TABLE 4

| | Maximum absorption wavelength | Color optical density | Degree of deterioration | Degree of coloration (ΔYI) |
|---|---|---|---|---|
| Ex. 20 | 574 nm | 0.92 | 10% | 3.1 |
| C. Ex. 5 | 574 nm | 0.92 | 23% | 4.9 |

Ex.: Example,
C. Ex.: Comparative Example

TABLE 5

| | Maximum absorption wavelength | Color optical density | Degree of deterioration | Degree of coloration (ΔYI) |
|---|---|---|---|---|
| Ex. 21 | 568 nm | 0.86 | 16% | 5.1 |
| C. Ex. 6 | 568 nm | 0.87 | 35% | 8.2 |

Ex.: Example,
C. Ex.: Comparative Example

Example 22

A monomer composition was obtained by mixing together 10 parts by mass of the purified urethane acrylate monomer obtained in Example 14, 10 parts by mass of glycidyl methacrylate, 10 parts by mass of trimethylolpropane trimethacrylate, 10 parts by mass of polyethylene glycol diacrylate (average molecular weight of ethylene glycol chain of 400) and 60 parts by mass of 2,2-bis(4-methacryloyloxypentaethoxyphenyl)propane as components of the monomer composition completely under agitation. 2 parts by mass of a photochromic compound represented by the following structural formula (A) was added to 100 parts by mass of this monomer composition, and then 0.5 part by mass of CGI1850 {mixture of 1-hydroxycyclohexylphenyl ketone and bis(2,6-dimethoxybenzoyl)-2,4,4-trimethyl-pentylphosphine oxide (weight ratio of 1:1)} as a photopolymerization initiator was added to the resulting mixture.

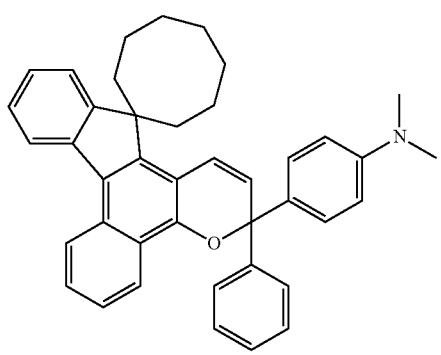

(A)

5 parts by mass of bis(1,2,2,6,6-pentamethyl-4-piperidyl) sebacate (stabilizer), 7 parts by mass of γ-methacryloyloxypropyl trimethoxysilane (adhesive component) and 3 parts by mass of N-methyldiethanolamine (adhesive component) were added to and fully mixed with the above mixture as other components to obtain a photochromic composition. This photochromic composition was applied to CR39 which is an allyl resin plastic lens and photopolymerized to obtain a photochromic cured product having a 40 μm-thick cured film. The photochromic properties and weather resistance of this photochromic cured product were evaluated. The deterioration promotion time is 100 hours. The measurement results are shown in Table 6.

Comparative Example 7

As comparison to Example 22, a photochromic composition and a photochromic cured product were obtained in the same manner as in Example 22 except that an unpurified urethane acrylate monomer (acid value of 1.59 mgKOH/g) was used. The evaluation results of photochromic properties and weather resistance are shown in Table 6.

TABLE 6

|  | Maximum absorption wavelength | Color optical density | Degree of deterioration | Degree of coloration (ΔYI) |
|---|---|---|---|---|
| Ex. 22 | 582 nm | 1.02 | 38% | 5.9 |
| C. Ex. 7 | 582 nm | 1.04 | 80% | 8.2 |

Ex.: Example,
C. Ex.: Comparative Example

It can be said from the results of Examples 18 to 22 and Comparative Examples 4 to 7 that photochromic cured products obtained by using the urethane acrylate monomers of the present invention have a lower degree of deterioration and a lower degree of coloration than photochromic cured products obtained by using unpurified urethane acrylate monomers and therefore are excellent in weather resistance.

Effect of the Invention

According to the present invention, a urethane (meth) acrylate monomer having a low acid value and containing little high-molecular weight impurity can be easily produced. Since the obtained urethane (meth) acrylate monomer has an extremely low content of an acid component, a deterioration reaction is suppressed. Therefore, the storage stability of the urethane (meth) acrylate monomer becomes high. Since a cured product obtained by using the urethane (meth) acrylate monomer has an extremely low content of an impurity, it has high quality with little discoloration and coloration. Further, even when the urethane (meth) acrylate monomer and a photochromic compound are used in combination, the weather resistance of the photochromic compound can be improved by employing the process of the present invention.

The invention claimed is:

1. A urethane (meth)acrylate monomer, which comprises a urethane (meth)acrylate monomer represented by the following formula (I):

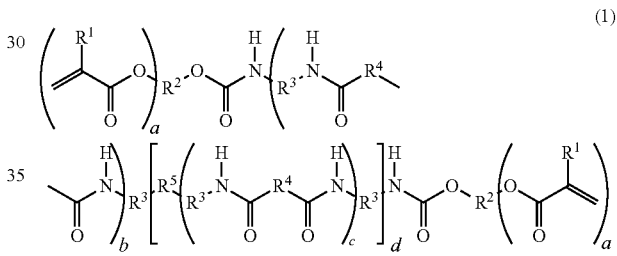

(1)

wherein, each a is independently an integer of 1 to 3, b, c and d are each independently an integer of 0 to 100, $R^1$ is a hydrogen atom or methyl group, $R^2$ is a divalent to tetravalent, aliphatic hydrocarbon group which may have a substituent, $R^3$ is a divalent organic residue selected from a divalent group having an aromatic ring, a divalent group having an aliphatic ring and an alkylene group, $R^4$ is a divalent organic residue selected from a divalent group having a polyether structure, a divalent group having a polycarbonate structure and a divalent group having a polyester structure, and $R^5$ is a divalent group having a urea bond or a divalent group having a urethane bond;

water; and an acid, wherein the content of water is greater than zero and not more than 700 ppm (mass) and the content of the acid is such that the acid value of the urethane (meth) acrylate monomer is not more than 0.2 mgKOH/g.

2. The urethane (meth)acrylate monomer according to claim 1, wherein the content of an insoluble component in a solution of 1 mass % of the urethane (meth)acrylate monomer in tetrahydrofuran is not more than 0.1 mass % based on the urethane (meth)acrylate monomer and the content of a high-molecular weight component having an average molecular weight which is 3 times or more that of the urethane (meth)acrylate monomer is less than 0.3 mass %.

3. The urethane (meth)acrylate monomer according to claim 1, wherein the urethane (meth)acrylate monomer has a polymerization shrinkage factor of less than 15% when it is cured.

4. A process of producing a urethane (meth)acrylate monomer, comprising the steps of:
(1) contacting a first solution of a urethane (meth)acrylate monomer comprising a urethane (meth)acrylate monomer and an organic solvent and having an acid value of more than 0.2 mgKOH/g to a water-containing adsorbent capable of adsorbing the acid component to obtain a second solution of a urethane (meth)acrylate monomer comprising the urethane (meth)acrylate monomer, the organic solvent and more than 5,000 ppm (mass) of water based on the urethane (meth)acrylate monomer and having an acid value of not more than 0.2 mgKOH/g;
(2) contacting the second solution to a dehydrating agent to obtain a third solution of a urethane (meth)acrylate monomer comprising the urethane (meth)acrylate monomer, the organic solvent and not more than 5,000 ppm (mass) of water based on the urethane (meth)acrylate monomer and having an acid value of not more than 0.2 mgKOH/g; and
(3) removing the organic solvent from the third solution.

5. The process of producing a urethane (meth)acrylate monomer according to claim 4, wherein an organic solvent having no active hydrogen is used as the organic solvent.

6. The process of producing a urethane (meth)acrylate monomer according to claim 4, wherein the water-containing adsorbent is an inorganic adsorbent having crystal water or adhesive water.

7. The process of producing a urethane (meth)acrylate monomer according to claim 4, wherein the amount of the organic solvent contained in the first solution is 100 to 500 parts by mass based on 100 parts by mass of the urethane (meth)acrylate monomer.

8. A monomer comprising the urethane (meth)acrylate monomer of claim 1.

9. An optical material obtained by curing the monomer of claim 8.

10. A photochromic composition comprising the monomer of claim 8 and at least one photochromic compound.

11. A photochromic cured product obtained by curing the photochromic composition of claim 10.

* * * * *